United States Patent
Zuo et al.

(10) Patent No.: US 9,416,647 B2
(45) Date of Patent: Aug. 16, 2016

(54) METHODS AND APPARATUS FOR CHARACTERIZATION OF HYDROCARBON RESERVOIRS

(71) Applicant: Schlumberger Technology Corporation, Sugar Land, TX (US)

(72) Inventors: Youxiang Zuo, Sugar Land, TX (US); Oliver C. Mullins, Ridgefield, CT (US); Chengli Dong, Sugar Land, TX (US); Dingan Zhang, Edmonton (CA); ChengGang Xian, Beijing (CN)

(73) Assignee: Schlumberger Technology Corporation, Sugar Land, TX (US)

( * ) Notice: Subject to any disclaimer, the term of this patent is extended or adjusted under 35 U.S.C. 154(b) by 743 days.

(21) Appl. No.: 13/754,549

(22) Filed: Jan. 30, 2013

(65) Prior Publication Data

US 2013/0197808 A1    Aug. 1, 2013

Related U.S. Application Data

(60) Provisional application No. 61/592,625, filed on Jan. 31, 2012.

(51) Int. Cl.
*E21B 49/08*    (2006.01)
*E21B 47/00*    (2012.01)
(Continued)

(52) U.S. Cl.
CPC ............... *E21B 47/00* (2013.01); *E21B 49/10* (2013.01); *G06F 17/00* (2013.01); *E21B 49/00* (2013.01); *G06F 19/704* (2013.01)

(58) Field of Classification Search
CPC ................................ E21B 47/00; G06F 17/00
USPC ............................................................ 702/6
See application file for complete search history.

(56) References Cited

U.S. PATENT DOCUMENTS

| 4,994,671 | A  | 2/1991  | Safinya et al.  |
| 6,501,072 | B2 | 12/2002 | Mullins et al.  |

(Continued)

FOREIGN PATENT DOCUMENTS

| WO | WO 2011007268 A1 * | 1/2011 | ............. E21B 47/10 |
| WO | 2012042397 A2      | 4/2012 |                          |

OTHER PUBLICATIONS

J.X. Wang and J.S. Buckley; "A Two-Component Solubility Model of the Onset of Asphaltene Flocculation in Crude Oils"; 2001; Energy and Fuels; vol. 15; pp. 1004-1012.*

(Continued)

*Primary Examiner* — Mischita Henson
*Assistant Examiner* — Christine Liao
(74) *Attorney, Agent, or Firm* — Kenneth L. Kincaid

(57) ABSTRACT

A methodology performs downhole fluid analysis at multiple measurement stations within a wellbore traversing a reservoir to determine gradients of compositional components and other fluid properties. A model is used to predict concentrations of a plurality of high molecular weight solute part class-types at varying reservoir locations. Such predictions are compared against downhole measurements to identify the best matching solute part class-type. If the best-matching class type corresponds to at least one predetermined asphaltene component, phase stability of asphaltene in the reservoir fluid at a given depth is evaluated using equilibrium criteria involving an oil rich phase and an asphaltene rich phase of respective components of the reservoir fluid at the given depth. The result of the evaluation of asphaltene rich phase stability is used for reservoir analysis. The computational analysis that evaluates asphaltene rich phase stability can also be used in other reservoir understanding workflows and in reservoir simulation.

18 Claims, 10 Drawing Sheets

(51) Int. Cl.
*G06F 19/00* (2011.01)
*G06F 17/00* (2006.01)
*E21B 49/10* (2006.01)
*E21B 49/00* (2006.01)

(56) References Cited

U.S. PATENT DOCUMENTS

| | | | |
|---|---|---|---|
| 7,081,615 | B2 | 7/2006 | Betancourt et al. |
| 7,822,554 | B2 | 10/2010 | Zuo et al. |
| 7,920,970 | B2 | 4/2011 | Zuo et al. |
| 7,996,154 | B2 | 8/2011 | Zuo et al. |
| 2008/0066536 | A1* | 3/2008 | Goodwin ............... E21B 49/10 73/152.24 |
| 2009/0312997 | A1* | 12/2009 | Freed ..................... E21B 49/00 703/10 |
| 2011/0088949 | A1 | 4/2011 | Zuo et al. |
| 2012/0232799 | A1 | 9/2012 | Zuo et al. |
| 2012/0296617 | A1 | 11/2012 | Zuo et al. |

OTHER PUBLICATIONS

Almehaideb, Reyadh A. et al., "EOS tuning to model full field crude oil properties using multiple well fluid PVT analysis," Journal of Petroleum Science and Engineering, vol. 26, Issues 1-4, pp. 291-300, 2000.
Betancourt, S.S., Dubost, F.X., Mullins, O.C., Cribbs, M.E., Creek. J.L., Mathews, S.G., "Predicting Downhole Fluid Analysis Logs to Investigate Reservoir Connectivity", IPTC 11488, presented at International Petroleum Technology Conference in Dubai, U.A.E., Dec. 4-6, 2007.
Diallo, M.S., Cagin, T., Fanion, J.L., and Goddard 111, W.A., "Thermodynamic Properties of Asphaltenes: A Predictive Approach Based on Computer Assisted Structure Elucidation and Atomistic Simulations", in book edited by Yen, T.F., and Chingarian, G.V., Asphaltenes and Asphalts. 2. Developments in Petroleum Scienece, 40 B, Elsevier Science B. V., (2000).
Hirschberg, Avraham, "Role of Asphaltenes in Compositional Grading of a Reservoir's Fluid Column," SPE 1317, Journal of Petroleum Technology, Jan. 1958, pp. 89-94.
Indo, K, Ratulowski, J., Dindoruk, B., Gao, J. , Zuo, J., Mullins, O.C., Asphaltene Nanoaggregates Measured in a Live Crude Oil by Centrifugation, Energy Fuels, 2009, 23 (9), pp. 4460-4469, DOI: 10.1021/ef900369r.
Khan, S.A., Al-Marhoun, MA., Duffuaa, S.O., and Abu-Khamsin, S.A. 1987. Viscosity Correlations for Saudi Arabian Crude Oils. SPE Paper 15720 presented at the Fifth SPE Middle East Conference held in Manama, Bahrain, Mar. 7-10, 1987.
Li "Rapid Flash Calculations for Compositional Simulation," SPE Reservoir Evaluation and Engineering, Oct. 2006.
Lin, M.S., Lunsford, K.M., Llover, C.J., Davison, R.R., Bullin, J.A. 1995. The effects of asphaltenes on the chemical and physical characteristics of asphalt. In Shu, EY, and Mullins, O,C., editors. Asphaltenes: fundamentals and applications. New York, Plenum Press, 1995, pp. 155-176.
Luo, P. and Gu, Y. 2006. Effects of asphaltene content on the heavy oil viscosity at different temperature. Fuel86: 1069-1078.
Mohammadi, A.H., and Richon, D., "A Monodisperse Thermodynamic Model for Estimating Asphaltene Precipitation", AIChE Journal, 53(11), 2940 -2947(2007).
Mooney, M. 1951. The viscosity of a concentrated suspension of spherical particles. J Colloid Science 6:162-170.
Mullins D.C., Betancourt S.S., Cribbs, M.E., Creek J.L., Dubost, F.X., Andrews, A Ballard, Venkataramanan, L., "Asphaltene Gravitational Gradient in a Deepwater Reservoir as Determined by Downhole Fluid Analysis", SPE 106375, 2007.
Pal, R., and Rhodes, E. 1989. Viscosity/concentration relationships for emulsions. Journal of Rheology33: 1021-1045.
Ting, P.O., Hirasaki, G.J., and Chapman, W.G, "Modeling of Asphaltene Phase Behavior with the SAFT Equation of State", Pet. Sci. Technol. 2003, 21, 647.
Vaidya, S. N., and Kennedy, G. C., "Compressibility of 18 Molecular Organic Solids to 45 kbar", J. Chern. Phys., 55(3), 978-992 (1971).
Vargas, P.M., Gonzalez, D.L., Creek, J.L., Wang, J., Buckley, J., Hirasaki, G.J., and Chapman, W.G., "Development of a General Method for Modeling Asphaltene Stability", Energy & Fuels, 23, 1147-1154 (2009).
Wilhelms, A. and Larter, S.R., "Origin of tar mats in petroleum reservoirs, Part I: Introduction and Case Studies," Marine and Petroleum Geology 1994 vol. 11 No. 4, 0264-8172/94/04/0418-24, pp. 418-441.
Wilhelms, A. and Larter, S.R., "Origin of tar mats in petroleum reservoirs. Part II: formation mechanisms for tar mats," Marine and Petroleum Geology 1994 vol. 11 No. 4, 0264-8172/94/04/0442-15, pp. 442-456.
Zuo, J.Y., Mullins, D.C., Freed, D., Zhang, D., "A Simple Correlation for Solubility Parameters of Live Reservoir Fluids" manuscript in preparation (2010).
Speight, J.G. and Plancher, H., "Molecular Models for Petroleum Asphaltencs and Implications for Asphalt Science and Technology", Proceedings of the futernational Symposium on the Chemistry of Bitumens, 1991.
Hirschberg, A, de Jong, L.N.J., Schipper, B.A., and Meijer, J.G., "Influence of Temperature and Pressure on Asphaltene Flocculation", Soc. Pet. Eng. J., 1984, 24, 283.
Zuo. J.Y., Mullins, D.C., Dong, C., Betancourt, S.S., Dubost, F.X., O'Keefe, M., Zhang, D., "Investigation of Formation Connectivity Using Asphaltene Gradient Log Predictions Coupled with Downhole Fluid Analysis", SPE 124264, presented at 2009 SPE Annual Technical Conference and Exhibition held in New Orleans, Louisiana, USA, Oct. 4-7, 2009.
Zuo, J.Y., Mullins, D.C., Dong, C., Zhang, D., O'Keefe, M., Dubost, F, Betancourt, S.S., Gao. 1., "Integration of Fluid Log Predictions and Downhole Fluid Analysis", SPE 122562, presented at 2009 SPE Asia Pacific Oil and Gas Conference and Exhibition held in Jakarta, Indonesia, Aug. 4-6, 2009.

\* cited by examiner

METHODS AND APPARATUS FOR CHARACTERIZATION OF HYDROCARBON RESERVOIRS

CROSS-REFERENCE TO RELATED APPLICATIONS

The present application claims priority from U.S. Provisional Pat. Appl. No. 61/592,625, filed on Jan. 31, 2012, entitled "Workflow for Tar Mat Formation and Asphaltene Instability in Hydrocarbon Reservoirs" herein incorporated by reference in its entirety.

BACKGROUND

1. Field

The present application relates to methods and apparatus for characterizing a hydrocarbon reservoir. More particularly, the present application relates to reservoir architecture understanding, although it is not limited thereto.

2. State of the Art

The statements made herein merely provide information related to the present disclosure and may not constitute prior art, and may describe some embodiments illustrating the invention.

Petroleum consists of a complex mixture of hydrocarbons of various molecular weights, plus other organic compounds. The exact molecular composition of petroleum varies widely from formation to formation. The proportion of hydrocarbons in the mixture is highly variable and ranges from as much as 97% by weight in the lighter oils to as little as 50% in the heavier oils and bitumens. The hydrocarbons in petroleum are mostly alkanes (linear or branched), cycloalkanes, aromatic hydrocarbons, or more complicated chemicals like asphaltenes. The other organic compounds in petroleum typically contain nitrogen, oxygen and sulfur, and trace amounts of metals such as iron, nickel, copper and vanadium.

Petroleum is usually characterized by SARA (Saturates/Aromatics/Resins/Asphaltenes) fractionation where asphaltenes are removed by precipitation with a paraffinic solvent and the deasphalted oil separated into saturates, aromatics and resins by chromatographic separation.

The saturates include alkanes and cycloalkanes. The alkanes, also known as paraffins, are saturated hydrocarbons with straight or branched chains which contain only carbon and hydrogen and have the general formula $C_nH_{2n+2}$. They generally have from 5 to 40 carbon atoms per molecule, although smaller amounts of shorter or longer molecules may be present in the liquid mixture. Further, the gas phase has ample smaller hydrocarbons. The alkanes include methane ($CH_4$), ethane ($C_2H_6$), propane ($C_3H_8$), i-butane ($iC_4H_{10}$), n-butane ($nC_4H_{10}$), i-pentane ($iC_5H_{12}$), n-pentane ($nC_5H_{12}$), hexane ($C_6H_{14}$), heptane ($C_7H_{16}$), octane ($C_8H_{18}$), nonane ($C_9H_{20}$), decane ($C_{10}H_{22}$), hendecane ($C_{11}H_{24}$)—also referred to as endecane or undecane, dodecane ($C_{12}H_{26}$), tridecane ($C_{13}H_{28}$), tetradecane ($C_{14}H_{30}$), pentadecane ($C_{15}H_{32}$) and hexadecane ($C_{16}H_{34}$). The cycloalkanes, also known as napthenes, are saturated hydrocarbons which have one or more carbon rings to which hydrogen atoms are attached according to the formula $C_nH_{2n}$. Cycloalkanes have similar properties to alkanes but have higher boiling points. The cycloalkanes include cyclopropane ($C_3H_6$), cyclobutane ($C_4H_8$), cyclopentane ($C_5H_{10}$), cyclohexane ($C_6H_{12}$), cycloheptane ($C_7H_{14}$), etc.

The aromatic hydrocarbons are unsaturated hydrocarbons which have one or more planar six-carbon rings called benzene rings, to which hydrogen atoms are attached with the formula $C_nH_m$ where $n \geq m$. They tend to burn with a sooty flame, and many have a sweet aroma. Some are carcinogenic. The aromatic hydrocarbons include benzene ($C_6H_6$) and derivatives of benzene as well as polyaromatic hydrocarbons.

Resins are the most polar and aromatic species present in the deasphalted oil and, it has been suggested, contribute to the enhanced solubility of asphaltenes in crude oil by solvating the polar and aromatic portions of the asphaltenic molecules and aggregates. In addition, the resins increase the liquid phase dielectric constant, further stabilizing the asphaltenes.

Asphaltenes are insoluble in n-alkanes (such as n-pentane or n-heptane) and soluble in toluene. The C:H ratio is approximately 1:1.2, depending on the asphaltene source. Unlike most hydrocarbon constituents, asphaltenes typically contain a few percent of other atoms (called heteroatoms), such as sulfur, nitrogen, oxygen, vanadium and nickel. Heavy oils and tar sands contain much higher proportions of asphaltenes than do medium-API oils or light oils. Condensates are virtually devoid of asphaltenes. As far as asphaltene structure is concerned, experts agree that some of the carbon and hydrogen atoms are bound in ring-like, aromatic groups, which also contain the heteroatoms. Alkane chains and cyclic alkanes contain the rest of the carbon and hydrogen atoms and are linked to the ring groups. Within this framework, asphaltenes exhibit a range of molecular weight and composition. Asphaltenes have been shown to have a distribution of molecular weight in the range of 300 to 1400 g/mol with an average of about 750 g/mol. This is compatible with a molecule contained seven or eight fused aromatic rings, and the range accommodates molecules with four to tens rings.

It is also known that asphaltene molecules aggregate to form nanoaggregates and clusters. The aggregation behavior depends on the solvent type. Laboratory studies have been conducted with asphaltene molecules dissolved in a solvent such as toluene. At extremely low concentrations (below $10^{-4}$ mass fraction), asphaltene molecules are dispersed as a true solution. At higher concentrations (on the order of $10^{-4}$ mass fraction), the asphaltene molecules stick together to form nanoaggregates. These nanoaggregates are dispersed in the fluid as a nanocolloid, meaning the nanometer-sized asphaltene particles are stably suspended in the continuous liquid phase solvent. At even higher concentrations (on the order of $5*10^{-3}$ mass fraction), the asphaltene nanoaggregates form clusters that remain stable as a colloid suspended in the liquid phase solvent. At higher concentrations, the asphaltene clusters flocculate to form clumps (or floccules) which are no longer in a stable colloid and precipitate out of the toluene solvent. In crude oil, asphaltenes exhibit a similar aggregation behavior. However, at the higher concentrations that cause asphaltene clusters to flocculate in toluene, stability can continue such that the clusters form a stable viscoelastic network in the crude oil. At even higher concentrations, the asphaltene clusters flocculate to form clumps (or floccules) which are no longer in a stable colloid and precipitate out of the crude oil.

Computer-based modeling and simulation techniques have been developed for estimating the properties and/or behavior of petroleum fluid in a reservoir of interest. Typically, such techniques employ an equation of state (EOS) model that represents the phase behavior of the petroleum fluid in the reservoir. Once the EOS model is defined, it can be used to compute a wide array of properties of the petroleum fluid of the reservoir, such as: gas-oil ratio (GOR) or condensate-gas ratio (CGR), density of each phase, volumetric factors and compressibility, heat capacity and saturation pressure (bubble or dew point). Thus, the EOS model can be solved to obtain saturation pressure at a given temperature. Moreover, GOR, CGR, phase densities, and volumetric factors are by-products of the EOS model. Transport properties, such as heat capacity or viscosity, can be derived from properties obtained from the EOS model, such as fluid composition. Furthermore, the EOS model can be extended with other reservoir evaluation techniques for compositional simulation of flow and production behavior of the petroleum fluid of the reservoir, as is well known in the art. For example, compositional simulations can be helpful in studying (1) depletion of a volatile oil or gas condensate reservoir where phase compositions and properties vary significantly with pressure below bubble or dew point pressures, (2) injection of non-equilibrium gas (dry or enriched) into a black oil reservoir to mobilize oil by vaporization into a more mobile gas phase or by condensation through an outright (single-contact) or dynamic (multiple-contact) miscibility, and (3) injection of $CO_2$ into an oil reservoir to mobilize oil by miscible displacement and by oil viscosity reduction and oil swelling.

In the past few decades, fluid homogeneity in a hydrocarbon reservoir has been assumed. However, there is now a growing awareness that fluids are often heterogeneous or compartmentalized in the reservoir. A compartmentalized reservoir consists of two or more compartments that effectively are not in hydraulic communication. Two types of reservoir compartmentalization have been identified, namely vertical and lateral compartmentalization. Vertical compartmentalization usually occurs as a result of faulting or stratigraphic changes in the reservoir, while lateral compartmentalization results from barriers to horizontal flow. Molecular and thermal diffusion, natural convection, biodegradation, adsorption, and external fluxes can also lead to non-equilibrium hydrocarbon distribution in a reservoir.

Conventionally, reservoir architecture (i.e., reservoir compartmentalization as well as non-equilibrium hydrocarbon distribution) has been determined utilizing pressure-depth plots and pressure gradient analysis with traditional straight-line regression schemes. This process may, however, be misleading as fluid compositional changes and compartmentalization give distortions in the pressure gradients, which result in erroneous interpretations of fluid contacts or pressure seals. Additionally, pressure communication does not prove flow connectivity.

U.S. Patent Publ. No. 2009/0312997 to Freed et al. provides a methodology for correlating composition data of live oil measured using a downhole fluid analyzer tool with predicted composition data to determine whether asphaltenes are in an equilibrium distribution within the reservoir. The methodology treats asphaltenes within the framework of polymer solution theory (Flory-Huggins-Zuo model). The methodology generates a family of curves that predicts asphaltene content as a function of height. The curves can be viewed as a function of two parameters, the volume and solubility of the asphaltene. The curves can be fit to measured asphaltene content as derived from the downhole fluid analysis tool. There can be uncertainty in the fitting process as asphaltene volume can vary widely. In these instances, it can be difficult to assess the accuracy of the Flory-Huggins-Zuo model and the resulting determinations based thereon at any given time, and thus know whether or not there is a need to acquire and analyze more downhole samples in order to refine or tune the Flory-Huggins-Zuo model and the resulting determinations based thereon.

U.S. Patent Publ. Nos. 2009/0312997 and 2012/0232799 assume that asphaltenes are kept in oil solutions in a single phase. However, asphaltenes can destabilize (i.e., experience phase instability) in the crude oil whereby the asphaltenes are no longer in a stable colloid and precipitate out of the crude oil. Such precipitation can result from natural processes which decrease oil (maltene) solubility of the asphaltenes in the reservoir, such as gas late stage gas charging. Such precipitation can also result from production processes which decrease oil (maltene) solubility of the asphaltenes in the reservoir, such gas injection or uplift. The precipitation of asphaltene can form a tar rich zone (e.g., a tar mat) in a reservoir. The tar rich zone(s) can significantly hinder production and can make the difference between an economically-viable field and an economically-nonviable field. Techniques to aid an operator to accurately identify issues of asphaltene precipitation and tar formation that leads reservoir compartments and their distribution in the reservoir can increase understanding of such reservoirs and ultimately raise production.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Embodiments are provided that accurately characterize compositional components and fluid properties at varying locations in a reservoir in order to allow for accurate reservoir architecture analysis, including detection of instability of the asphaltene rich phase whereby asphaltenes are no longer in a stable colloid and precipitate out of the petroleum fluid of the reservoir. Such detection can identify issues of tar formation that can lead to reservoir flow barriers and hinder production, for example, by impeding water drive or by precluding aquifer support by water injection. The reservoir architecture analysis can also include determining connectivity (or compartmentalization) and equilibrium hydrocarbon distribution (or non-equilibrium hydrocarbon distribution) in the reservoir of interest.

In accord with the present application, a downhole fluid analysis tool is employed to obtain and perform downhole fluid analysis of live oil samples at multiple measurement stations within a wellbore traversing a reservoir of interest. Such downhole fluid analysis measures compositional components and possibly other fluid properties of each live oil sample. The downhole measurements can be used in conjunction with an equation of state model to predict gradients of the compositional components as well as other fluid properties for reservoir analysis. A model is used to predict concentrations of a plurality of high molecular weight solute part class-types at varying locations in a reservoir. Such predictions are compared against the downhole measurements associated therewith to identify the best matching solute part class-type for reservoir analysis. In the event that the best-matching class type corresponds to at least one predetermined asphaltene component, phase stability of asphaltene in the petroleum fluid of the reservoir at a given depth is evaluated using equilibrium criteria involving an oil rich phase and an asphaltene rich phase of respective components of the petroleum fluid at the given depth. The result of the evaluation of asphaltene rich phase stability is used for reservoir analysis.

For example, if the phase of the asphaltenes is determined to be unstable at a given depth, the asphaltenes are no longer in a stable colloid and precipitate out of the reservoir fluid to form tar. Such tar formation can lead to flow barriers in the reservoir, which hinders production. Specifically, data defining the depths or intervals of the reservoir where the asphaltenes are unstable and form tar can be generated, stored and/or output to the user. Additional sampling and analysis of the oil column of the reservoir can be recommended (and performed) to confirm the phase instability of asphaltenes and possible implications of such instability during production, such as by gas injection or gas lift.

The computational analysis for evaluation of asphaltene rich phase stability can be part of a workflow for reservoir understanding that determines that the reservoir is connected and in thermal equilibrium or compartmentalized or not in thermodynamic equilibrium. The workflow can also determine whether or not to include one or more additional measurement stations (and possibly refine or tune the models of the workflow based on the measurements for the additional measurement stations) for better accuracy and confidence in the fluid measurements and predictions that are used for the reservoir analysis. The computational analysis for evaluation of asphaltene rich phase stability can also be part of other reservoir understanding workflows and/or reservoir simulation.

In one embodiment, the equilibrium criteria, used to evaluate stability of the asphaltene rich phase, are based upon the concentration of a set of components of the petroleum fluid as a function of depth in the reservoir, whereby the set of components include at least one asphaltene component. The component concentrations can be derived from downhole fluid analysis and/or from an equation of state model. The equilibrium criteria are preferably defined by a relationship of the form $$x_i^{oil}\gamma_i^{oil} = x_i^{asph}\gamma_i^{asph},$$

where the subscript i corresponds to the respective component of the petroleum fluid of the reservoir at the given depth, superscripts oil and asph correspond to the oil rich phase and asphaltene rich phase, respectively, of the component i at the given depth, $x_i^{oil}$ is the mole fraction of the oil rich phase of component i of the petroleum fluid of the reservoir at the given depth, $\gamma_i^{oil}$ is the activity coefficient of the oil rich phase of component i of the petroleum fluid of the reservoir at the given depth, $x_i^{asph}$ is the mole fraction of the asphaltene rich phase of component i of the petroleum fluid of the reservoir at the given depth, and $\gamma_i^{asph}$ is the activity coefficient of the asphaltene rich phase of component i of the petroleum fluid of the reservoir at the given depth.

In another embodiment, the model used to predict concentrations of the plurality of high molecular weight solute part class-types is a Flory-Huggins-Zuo type solubility model that characterizes relative concentrations of a set of high molecular weight components as a function of depth as related to relative solubility, density and molar volume of the high molecular weight components of the set at varying depth. The solubility model treats the reservoir fluid as a mixture of two parts, the two parts being a solute part and a solvent part, the solute part comprising the set of high molecular weight components. The high molecular weight components of the solute part are preferably selected from the group including resins, asphaltene nanoaggregates, and asphaltene clusters. Preferred embodiments of such models are set forth in detail below.

The reservoir analysis can determine that asphaltene clusters are dispersed in a stable condition in the oil column. In this case, heavy oil or bitumen is expected in the oil column. Moreover, because asphaltene clusters are expected in the oil column, it is anticipated that a large density and viscosity gradients exist in the oil column, and a large API gravity increase exists in the oil column. In this case, one or more simple viscosity models can be used to characterize the viscosity of the heavy oil column. Preferred embodiments of such viscosity models are set forth in detail below.

Additional objects and advantages of the invention will become apparent to those skilled in the art upon reference to the detailed description taken in conjunction with the provided figures.

DETAILED DESCRIPTION

The particulars shown herein are by way of example and for purposes of illustrative discussion of the embodiments of the present application only and are presented in the cause of providing what is believed to be the most useful and readily understood description of the principles and conceptual aspects of the embodiments. In this regard, no attempt is made to show structural details of the embodiments of the present application in more detail than is necessary for the fundamental understanding of such embodiments. Further, like reference numbers and designations in the various drawings indicated like elements.

Figure 1A:
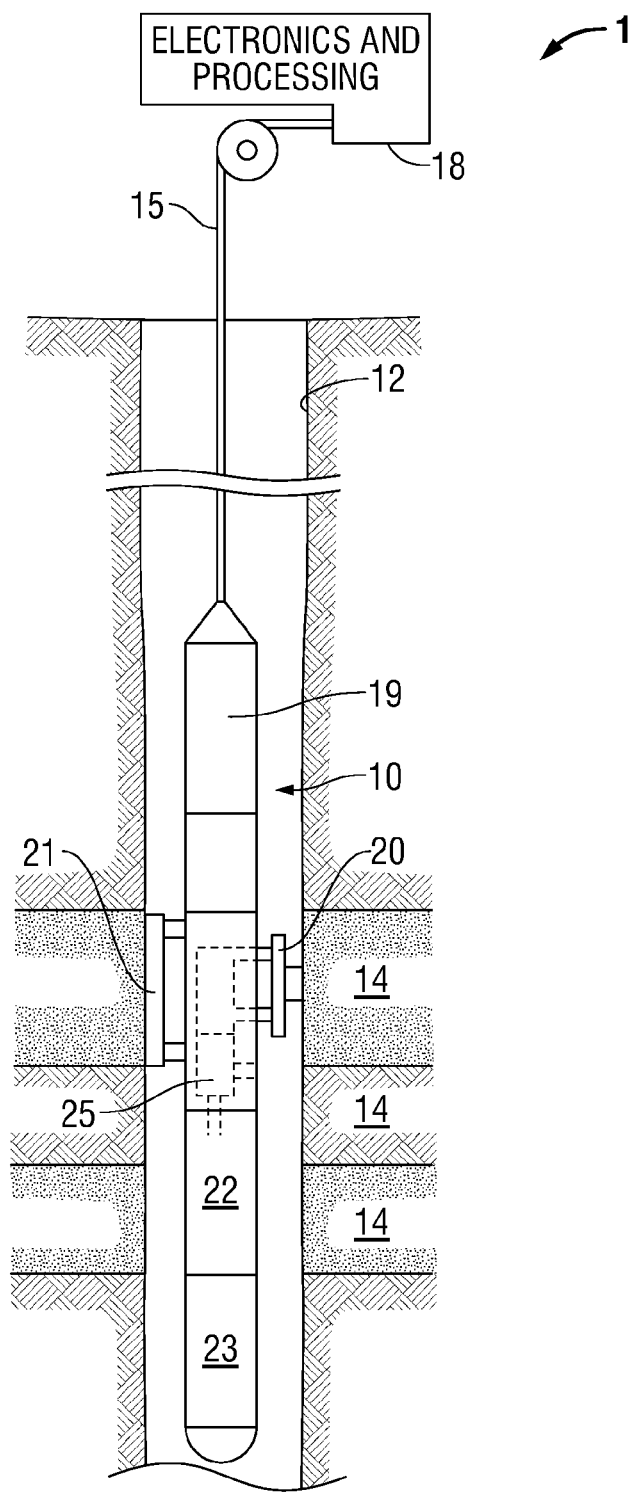
FIG. 1A is a schematic diagram of an exemplary petroleum reservoir analysis system in accordance with the present application.

FIG. 1A illustrates an exemplary petroleum reservoir analysis system 1 in which the present invention is embodied. The system 1 includes a borehole tool 10 suspended in the borehole 12 from the lower end of a typical multiconductor cable 15 that is spooled in a usual fashion on a suitable winch (not shown) on the formation surface. The cable 15 is electrically coupled to an electrical control system 18 on the formation surface. The tool 10 includes an elongated body 19 which carries a selectively extendable fluid admitting assembly 20 and a selectively extendable tool anchoring member 21 which are respectively arranged on opposite sides of the tool body. The fluid admitting assembly 20 is equipped for selectively sealing off or isolating selected portions of the wall of the borehole 12 such that fluid communication with the adjacent earth formation 14 is established. The fluid admitting assembly 20 and tool 10 include a flowline leading to a fluid analysis module 25. The formation fluid obtained by the fluid admitting assembly 20 flows through the flowline and through the fluid analysis module 25. The fluid may thereafter be expelled through a port (not shown) or it may be sent to one or more fluid collecting chambers 22 and 23 which may receive and retain the fluids obtained from the formation. With the assembly 20 sealingly engaging the formation 14, a short rapid pressure drop can be used to break the mudcake seal. Normally, the first fluid drawn into the tool will be highly contaminated with mud filtrate. As the tool continues to draw fluid from the formation 14, the area near the assembly 20 cleans up and reservoir fluid becomes the dominant constituent. The time required for cleanup depends upon many parameters, including formation permeability, fluid viscosity, the pressure differences between the borehole and the formation, and overbalanced pressure difference and its duration during drilling. Increasing the pump rate can shorten the cleanup time, but the rate must be controlled carefully to preserve formation pressure conditions.

The fluid analysis module 25 includes means for measuring the temperature and pressure of the fluid in the flowline. The fluid analysis module 25 derives properties that characterize the formation fluid sample at the flowline pressure and temperature. In the preferred embodiment, the fluid analysis module 25 measures absorption spectra and translates such measurements into concentrations of several alkane components and groups in the fluid sample. In an illustrative embodiment, the fluid analysis module 25 provides measurements of the concentrations (e.g., weight percentages) of carbon dioxide ($CO_2$), methane ($CH_4$), ethane ($C_2H_6$), the C3-C5 alkane group, the lump of hexane and heavier alkane components (C6+), and asphaltene content. The C3-C5 alkane group includes propane, butane, and pentane. The C6+ alkane group includes hexane ($C_6H_{14}$), heptane ($C_7H_{16}$), octane ($C_8H_{18}$), nonane ($C_9H_{20}$), decane ($C_{10}H_{22}$), hendecane ($C_{11}H_{24}$)—also referred to as endecane or undecane, dodecane ($C_{12}H_{26}$), tridecane ($C_{13}H_{28}$), tetradecane ($C_{14}H_{30}$), pentadecane ($C_{15}H_{32}$), hexadecane ($C_{16}H_{34}$), etc. The fluid analysis module 25 also provides a means that measures live fluid density ($\rho$) at the flowline temperature and pressure, live fluid viscosity ($\mu$) at flowline temperature and pressure (in cp), formation pressure, and formation temperature.

Control of the fluid admitting assembly 20 and fluid analysis module 25, and the flow path to the collecting chambers 22, 23 is maintained by the control system 18. As will be appreciated by those skilled in the art, the fluid analysis module 25 and the surface-located electrical control system 18 include data processing functionality (e.g., one or more microprocessors, associated memory, and other hardware and/or software) to implement the invention as described herein. The electrical control system 18 can also be realized by a distributed data processing system wherein data measured by the tool 10 is communicated (preferably in real time) over a communication link (typically a satellite link) to a remote location for data analysis as described herein. The data analysis can be carried out on a workstation or other suitable data processing system (such as a computer cluster or computing grid).

Formation fluids sampled by the tool 10 may be contaminated with mud filtrate. That is, the formation fluids may be contaminated with the filtrate of a drilling fluid that seeps into the formation 14 during the drilling process. Thus, when fluids are withdrawn from the formation 14 by the fluid admitting assembly 20, they may include mud filtrate. In some examples, formation fluids are withdrawn from the formation 14 and pumped into the borehole or into a large waste chamber (not shown) in the tool 10 until the fluid being withdrawn becomes sufficiently clean. A clean sample is one where the concentration of mud filtrate in the sample fluid is acceptably low so that the fluid substantially represents native (i.e., naturally occurring) formation fluids. In the illustrated example, the tool 10 is provided with fluid collecting chambers 22 and 23 to store collected fluid samples.

The system of FIG. 1A is adapted to make in situ determinations regarding hydrocarbon bearing geological formations by downhole sampling of reservoir fluid at one or more measurement stations within the borehole 12, conducting downhole fluid analysis of one or more reservoir fluid samples for each measurement station (including compositional analysis such as estimating concentrations of a plurality of compositional components of a given sample as well as other fluid properties), and relating the downhole fluid analysis to an equation of state (EOS) model of the thermodynamic behavior of the fluid in order to characterize the reservoir fluid at different locations within the reservoir. With the reservoir fluid characterized with respect to its thermodynamic behavior, fluid production parameters, transport properties, and other commercially useful indicators of the reservoir can be computed.

For example, the EOS model can provide the phase envelope that can be used to interactively vary the rate at which samples are collected in order to avoid entering the two-phase region. In other example, the EOS can provide useful properties in assessing production methodologies for the particular reserve. Such properties can include density, viscosity, and volume of gas formed from a liquid after expansion to a specified temperature and pressure. The characterization of the fluid sample with respect to its thermodynamic model can also be used as a benchmark to determine the validity of the obtained sample, whether to retain the sample, and/or whether to obtain another sample at the location of interest. More particularly, based on the thermodynamic model and information regarding formation pressures, sampling pressures, and formation temperatures, if it is determined that the fluid sample was obtained near or below the bubble line of the sample, a decision may be made to jettison the sample and/or to obtain sample at a slower rate (i.e., a smaller pressure drop) so that gas will not evolve out of the sample. Alternatively, because knowledge of the exact dew point of a retrograde gas condensate in a formation is desirable, a decision may be made, when conditions allow, to vary the pressure drawdown in an attempt to observe the liquid condensation and thus establish the actual saturation pressure.

Figure 1B:
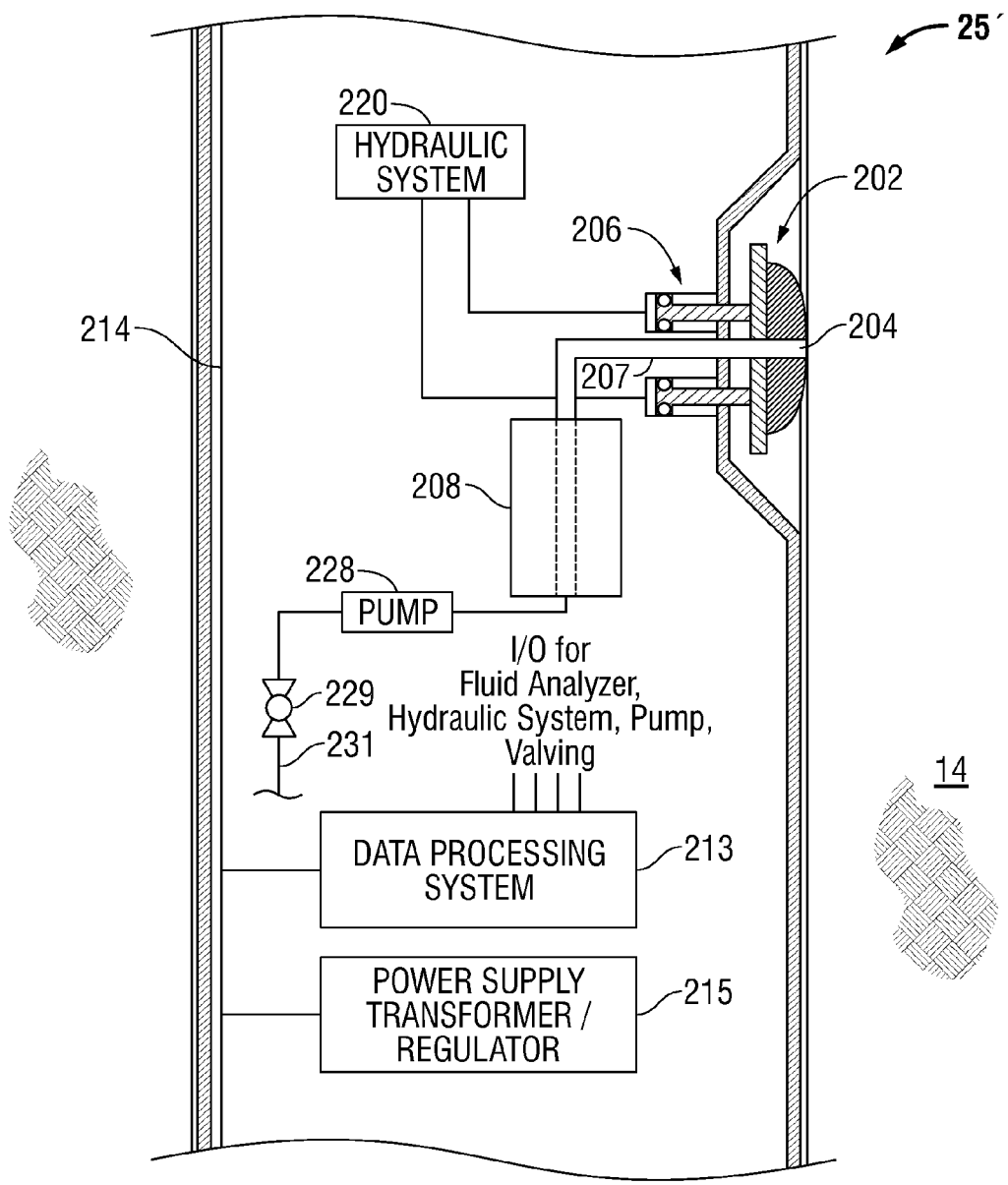
FIG. 1B is a schematic diagram of an exemplary fluid analysis module suitable for use in the borehole tool of FIG. 1A.
Figure 2A:
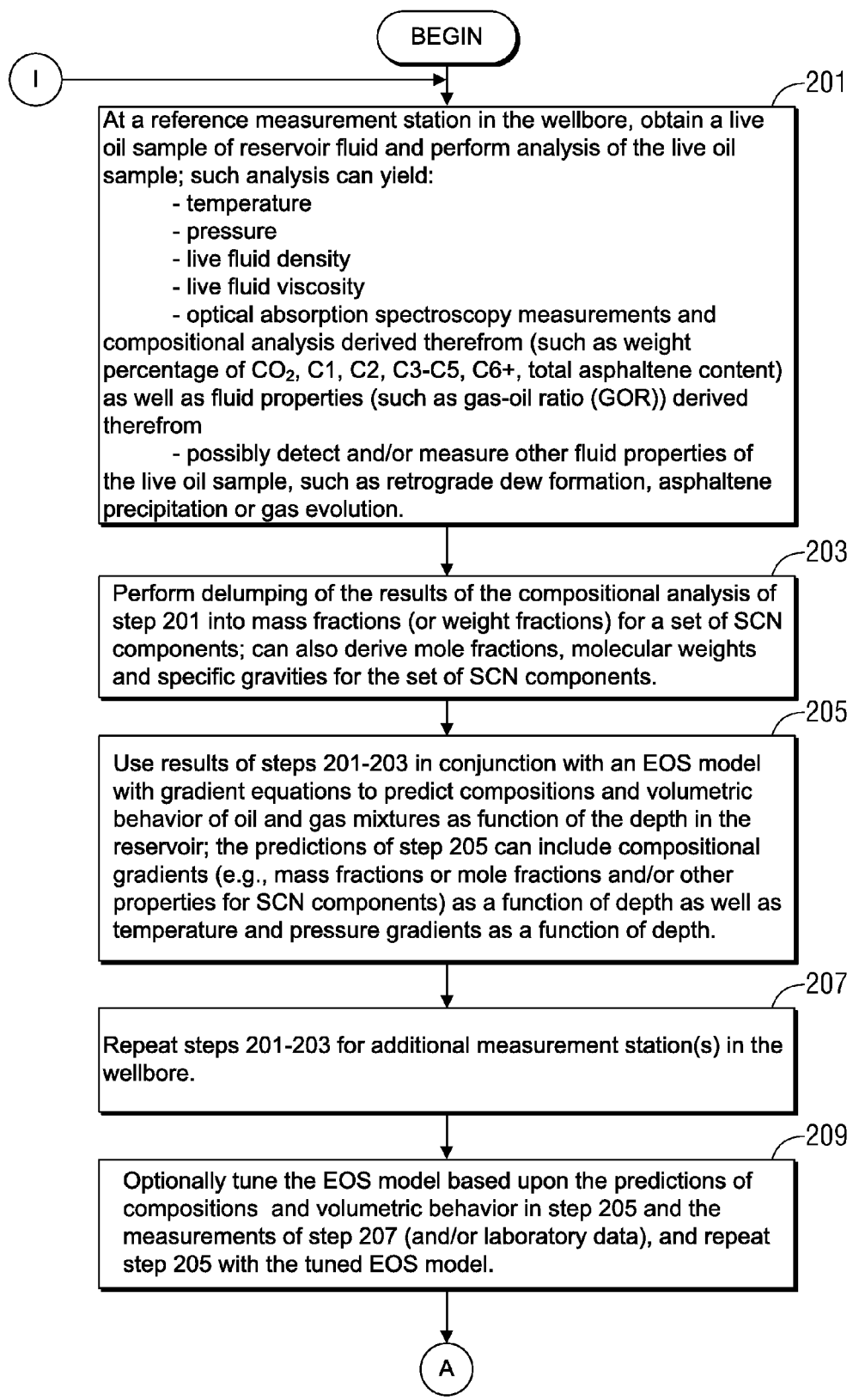
FIGS. 2A-2H, collectively, are a flow chart of data analysis operations that includes downhole fluid measurements at a number of different measurement stations within a wellbore traversing a reservoir or interest in conjunction with at least one solubility model that characterizes the relationship between solvent and solute parts of the reservoir fluids at different measurement stations. The solubility model is used to calculate a predicted value of the relative concentration of the solute part for at least one given measurement station for different solute class types. The predicted solute part concentration values are compared to corresponding solute part concentration values measured by the downhole fluid analysis to determine the best matching solute class type. In the event that the best-matching solute class type corresponds to at least one predetermined asphaltene component, phase stability of asphaltene in the reservoir fluids at a given depth is evaluated using equilibrium criteria involving an oil rich phase and an asphaltene rich phase of respective components of the petroleum fluid at the given depth. The result of the evaluation of stability of the asphaltene rich phase is used for reservoir analysis.
Figure 2B:
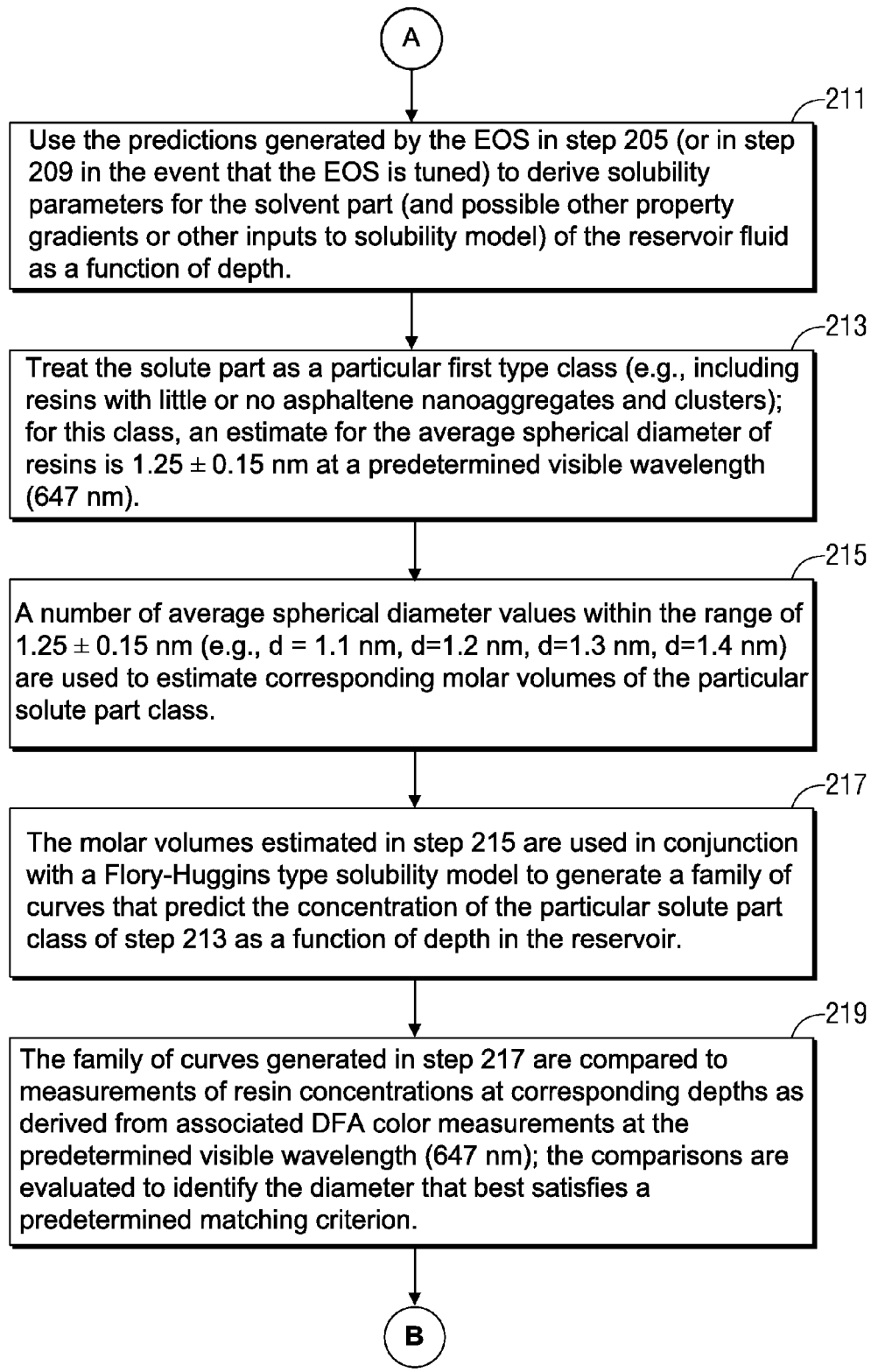
Figure 2C:
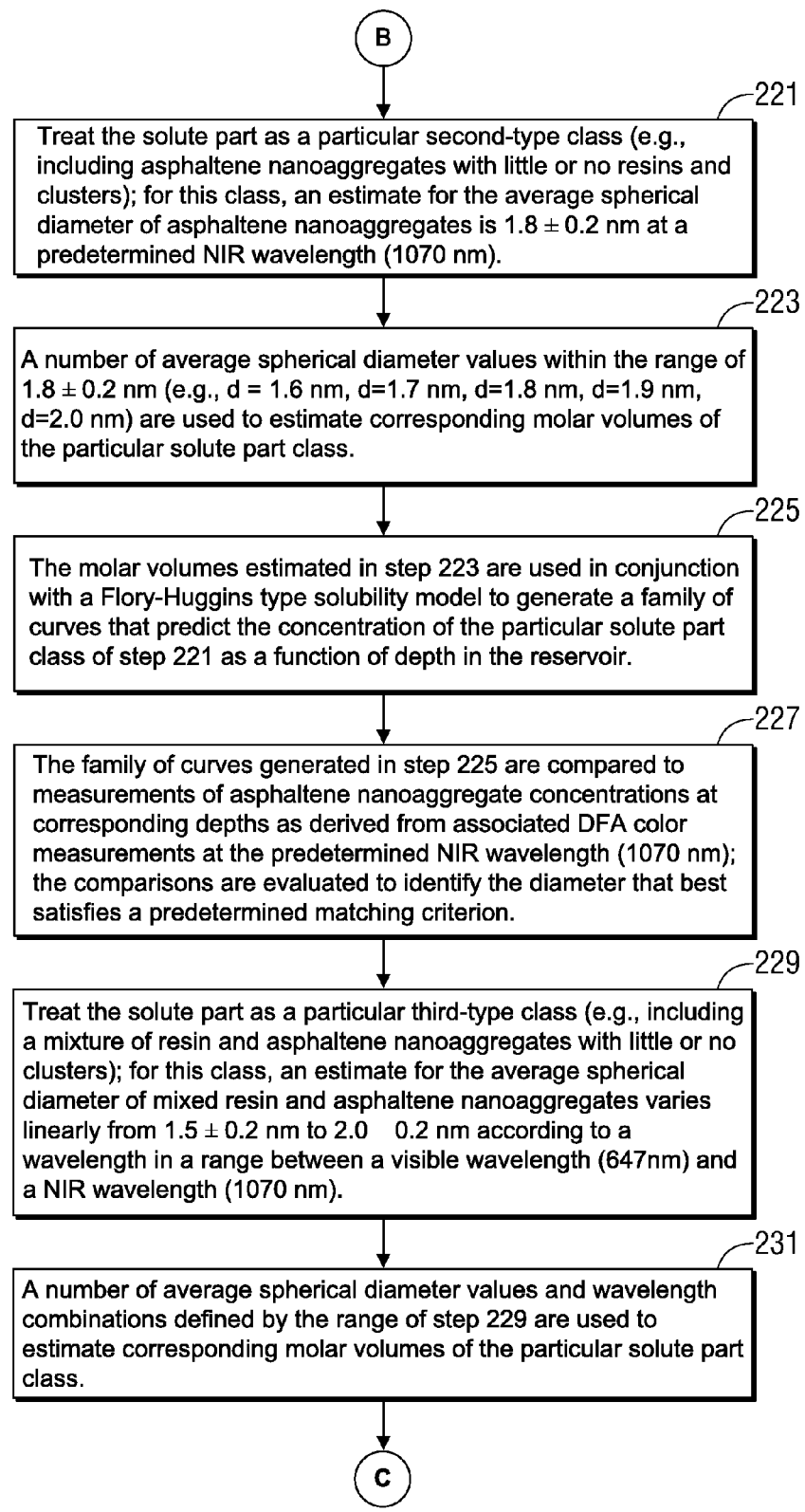
Figure 2D:
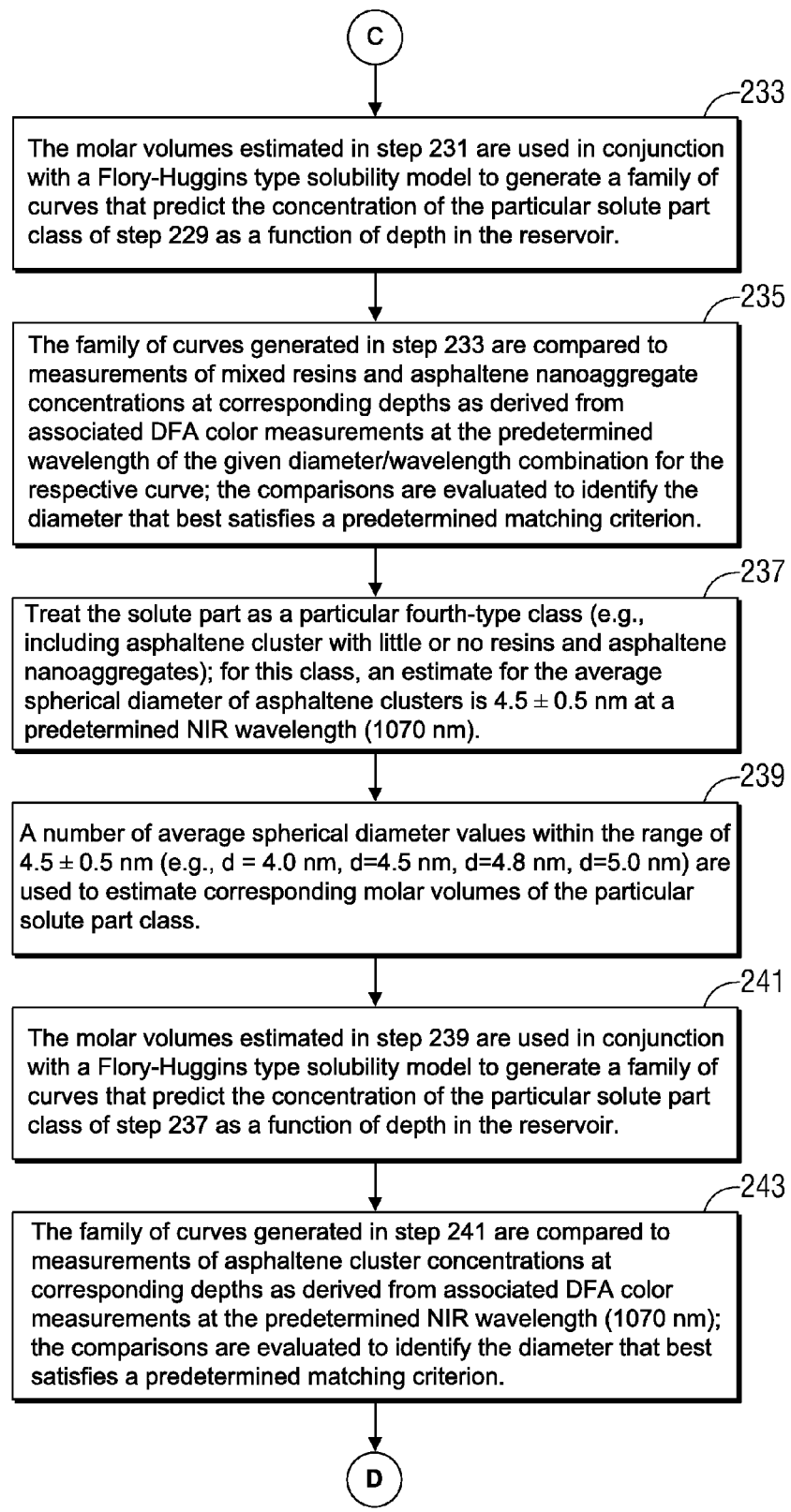
Figure 2E:
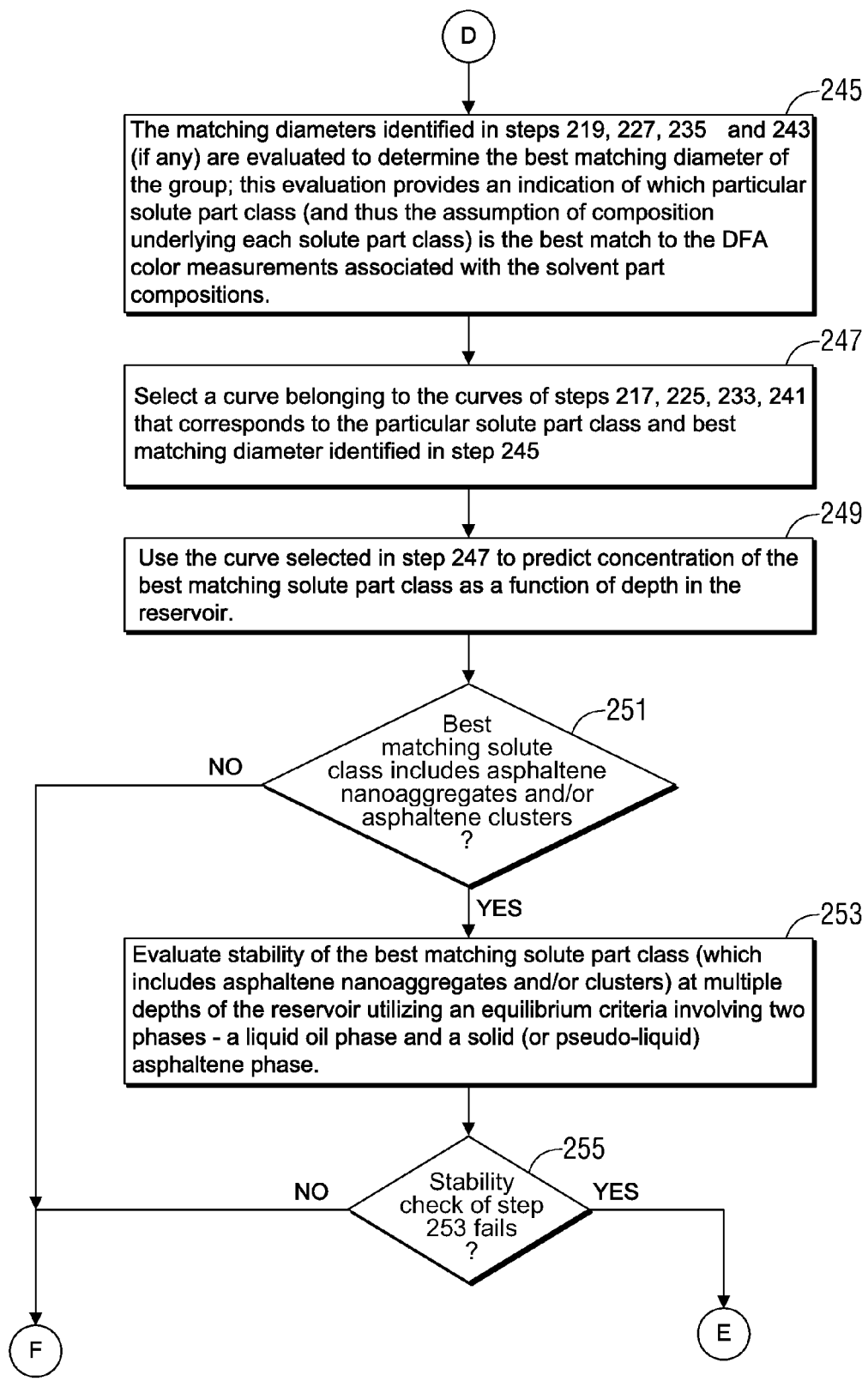
Figure 2F:
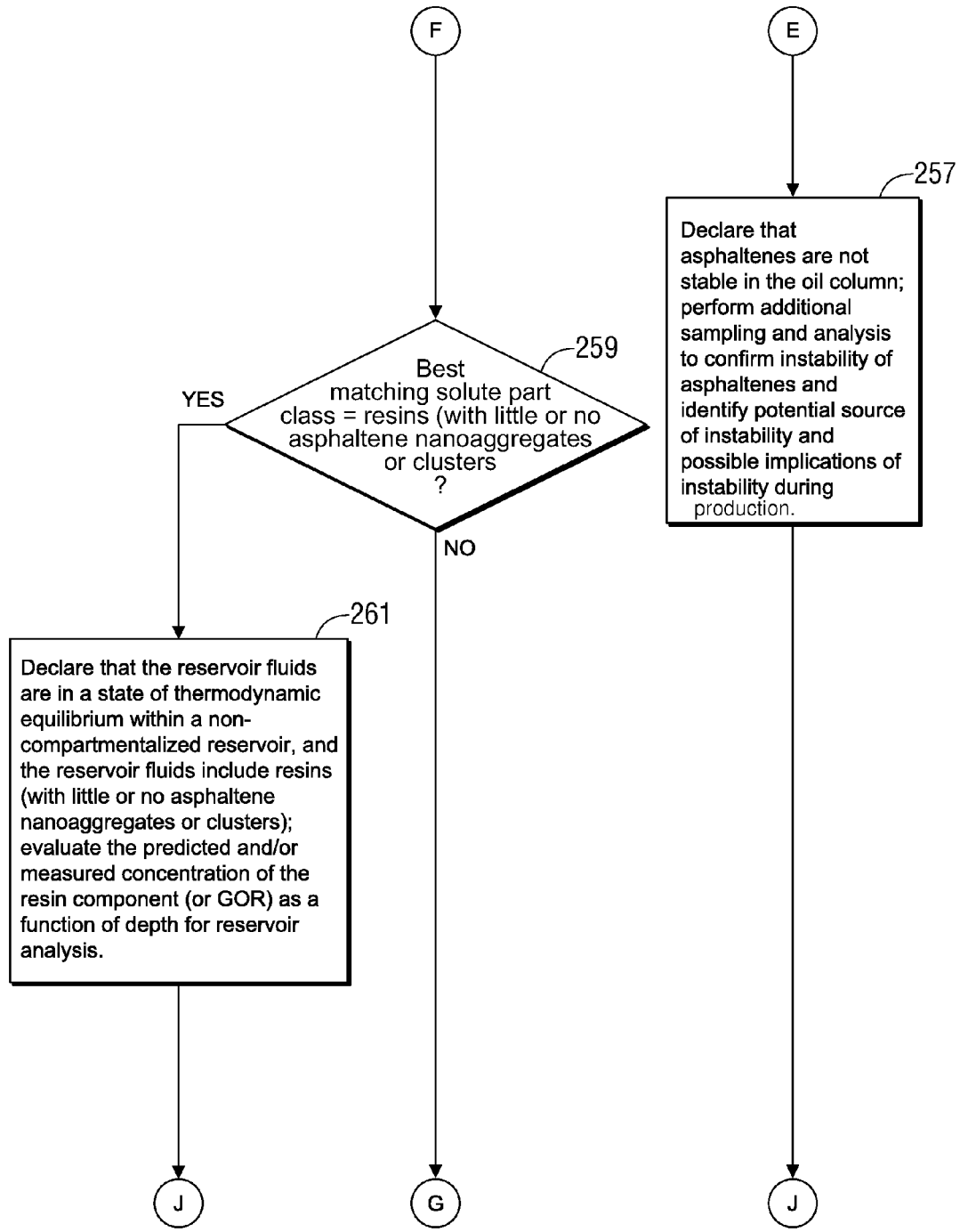
Figure 2G:
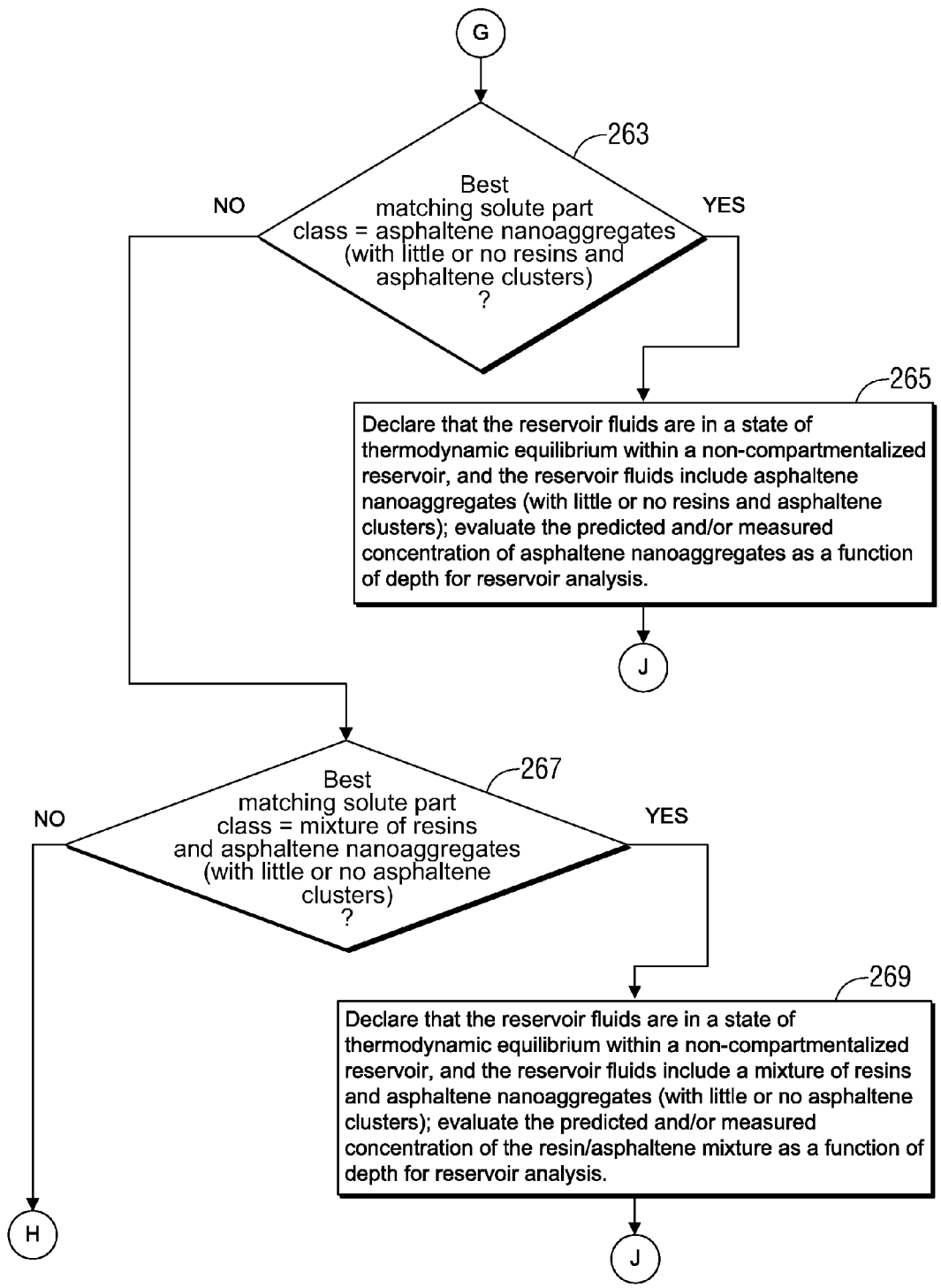
Figure 2H:
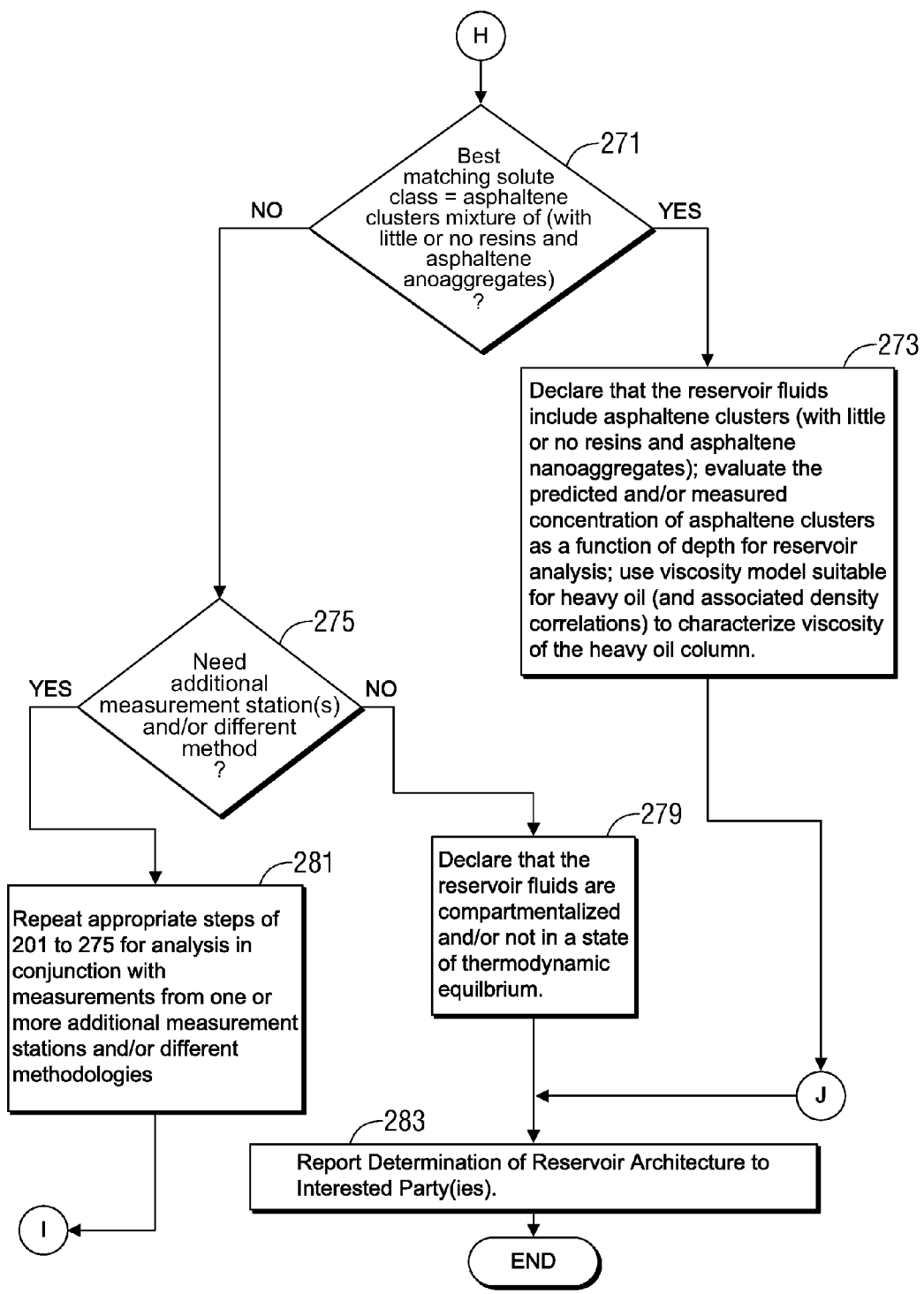

FIG. 1B illustrates an exemplary embodiment of the fluid analysis module 25 of FIG. 1A (labeled 25'), including a probe 202 having a port 204 to admit formation fluid therein. A hydraulic extending mechanism 206 may be driven by a hydraulic system 220 to extend the probe 202 to sealingly engage the formation 14 (FIG. 1A). In alternative implementations, more than one probe can be used or inflatable packers can replace the probe(s) and function to establish fluid connections with the formation and sample fluid samples.

The probe 202 can be realized by the Quicksilver Probe developed by Schlumberger. The Quicksilver Probe divides the fluid flow from the reservoir into two concentric zones, a central zone isolated from a guard zone about the perimeter of the central zone. The two zones are connected to separate flowlines with independent pumps. The pumps can be run at different rates to exploit filtrate/fluid viscosity contrast and permeability anistrotropy of the reservoir. Higher intake velocity in the guard zone directs contaminated fluid into the guard zone flowline, while clean fluid is drawn into the central zone. Fluid analyzers analyze the fluid in each flowline to determine the composition of the fluid in the respective flowlines. The pump rates can be adjusted based on such compositional analysis to achieve and maintain desired fluid contamination levels. The operation of the Quicksilver Probe efficiently separates contaminated fluid from cleaner fluid early in the fluid extraction process, which results in the obtaining clean fluid in much less time that compared to traditional formation testing tools.

The fluid analysis module 25' includes a flowline 207 that carries formation fluid from the port 204 through a fluid analyzer 208. The fluid analyzer 208 includes a light source that directs light to a sapphire prism disposed adjacent the flowline fluid flow. The reflection of such light is analyzed by a gas refractometer and dual fluorescence detectors. The gas refractometer qualitatively identifies the fluid phase in the flowline. At the selected angle of incidence of the light emitted from the diode, the reflection coefficient is much larger when gas is in contact with the window than when oil or water is in contact with the window. The dual fluorescence detectors detect free gas bubbles and retrograde liquid dropout to accurately detect single-phase fluid flow in the flowline 207. Fluid type is also identified. The resulting phase information can be used to define the difference between retrograde condensates and volatile oils, which can have similar GORs and live-oil densities. It can also be used to monitor phase-separation in real time and ensure single-phase sampling. The fluid analyzer 208 also includes dual spectrometers—a filter-array spectrometer and a grating-type spectrometer.

The filter-array spectrometer of the analyzer 208 includes a broadband light source providing broadband light that passes along optical guides and through an optical chamber in the flowline to an array of optical density detectors that are designed to detect narrow frequency bands (commonly referred to as channels) in the visible and near-infrared spectra as described in U.S. Pat. No. 4,994,671 to Safinya et al., herein incorporated by reference in its entirety. Preferably, these channels include a subset of channels that detect water-absorption peaks (which are used to characterize water content in the fluid) as well as a dedicated channel corresponding to the absorption peak of $CO_2$ with dual channels above and below this dedicated channel that subtract out the overlapping spectrum of hydrocarbon and small amounts of water (which are used to characterize $CO_2$ content in the fluid). The filter-array spectrometer also employs optical filters that provide for identification of the color (also referred to as "optical density" or "OD") of the fluid in the flowline. Such color measurements supports fluid identification, determination of asphaltene content and PH measurement. Mud filtrates or other solid materials generate noise in the channels of the filter-array spectrometer. Scattering caused by these particles is independent of wavelength. In the preferred embodiment, the effect of such scattering can be removed by subtracting a nearby channel. The grating-type spectrometer of the analyzer 208 is designed to detect channels in the near-infrared spectra (preferably between 1600-1800 nm) where reservoir fluid has absorption characteristics that reflect molecular structure.

The analyzer 208 also includes a pressure sensor for measuring pressure of the formation fluid in the flowline 207, a temperature sensor for measuring temperature of the formation fluid in the flowline 207, and a density sensor for measuring live fluid density of the fluid in the flowline 207. In the preferred embodiment, the density sensor is realized by a vibrating sensor that oscillates in two perpendicular modes within the fluid. Simple physical models describe the resonance frequency and quality factor of the sensor in relation to live fluid density. Dual-mode oscillation is advantageous over other resonant techniques because it minimizes the effects of pressure and temperature on the sensor through common mode rejection. In addition to density, the density sensor can also provide a measurement of live fluid viscosity from the quality factor of oscillation frequency. Note that live fluid viscosity can also be measured by placing a vibrating object in the fluid flow and measuring the increase in line width of any fundamental resonance. This increase in line width is related closely to the viscosity of the fluid. The change in frequency of the vibrating object is closely associated with the mass density of the object. If density is measured independently, then the determination of viscosity is more accurate because the effects of a density change on the mechanical resonances are determined. Generally, the response of the vibrating object is calibrated against known standards. The analyzer 208 can also measure resistivity and pH of fluid in the flowline 207. In the preferred embodiment, the fluid analyzer 208 is realized by the Insitu Fluid Analyzer commercially available from Schlumberger. In other exemplary implementations, the flowline sensors of the analyzer 208 may be replaced or supplemented with other types of suitable measurement sensors (e.g., NMR sensors, capacitance sensors, etc.). Pressure sensor(s) and/or temperature sensor(s) for measuring pressure and temperature of fluid drawn into the flowline 207 can also be part of the probe 202.

A pump 228 is fluidly coupled to the flowline 207 and is controlled to draw formation fluid into the flowline 207 and possibly to supply formation fluid to the fluid collecting chambers 22 and 23 (FIG. 1A) via valve 229 and flowpath 231 (FIG. 1B).

The fluid analysis module 25' includes a data processing system 213 that receives and transmits control and data signals to the other components of the module 25' for controlling operations of the module 25'. The data processing system 213 also interfaces to the fluid analyzer 208 for receiving, storing and processing the measurement data generated therein. In the preferred embodiment, the data processing system 213 processes the measurement data output by the fluid analyzer 208 to derive and store measurements of the hydrocarbon composition of fluid samples analyzed insitu by the fluid analyzer 208, including flowline temperature;
flowline pressure;
live fluid density ($\rho$) at the flowline temperature and pressure;
live fluid viscosity ($\mu$) at flowline temperature and pressure;
concentrations (e.g., weight percentages) of carbon dioxide ($CO_2$), methane ($CH_4$), ethane ($C_2H_6$), the $C_3$-$C_5$ alkane group, the lump of hexane and heavier alkane components (C6+), and asphaltene content;
GOR; and
possibly other parameters (such as API gravity, oil formation volume factor (Bo), etc.)

Flowline temperature and pressure is measured by the temperature sensor and pressure sensor, respectively, of the fluid analyzer 208 (and/or probe 202). In the preferred embodiment, the output of the temperature sensor(s) and pressure sensor(s) are monitored continuously before during and after sample acquisition to derive the temperature and pressure of the fluid in the flowline 207. The formation temperature is not likely to deviate substantially from the flowline temperature at a given measurement station and thus can be estimated as the flowline temperature at the given measurement station in many applications. Formation pressure can be measured by the temperature sensor and pressure sensor, respectively, of the fluid analyzer 208 in conjunction with the downhole fluid sampling and analysis at a particular measurement station after buildup of the flowline to formation pressure.

Live fluid density ($\rho$) at the flowline temperature and pressure is determined by the output of the density sensor of the fluid analyzer 208 at the time the flowline temperature and pressure is measured.

Live fluid viscosity ($\mu$) at flowline temperature and pressure is derived from the quality factor of the density sensor measurements at the time the flowline temperature and pressure is measured.

The measurements of the hydrocarbon composition of fluid samples are derived by translation of the data output by spectrometers of the fluid analyzer 208.

The GOR is determined by measuring the quantity of methane and liquid components of crude oil using near infrared absorption peaks. The ratio of the methane peak to the oil peak on a single phase live crude oil is directly related to GOR.

The fluid analysis module 25' can also detect and/or measure other fluid properties of a given live oil sample, including retrograde dew formation, asphaltene precipitation and/or gas evolution.

The fluid analysis module 25' also includes a tool bus 214 that communicates data signals and control signals between the data processing system 213 and the surface-located system 18 of FIG. 1A. The tool bus 214 can also carry electrical power supply signals generated by a surface-located power source for supply to the module 25', and the module 25' can include a power supply transformer/regulator 215 for transforming the electric power supply signals supplied via the tool bus 214 to appropriate levels suitable for use by the electrical components of the module 25'.

Although the components of FIG. 1B are shown and described above as being communicatively coupled and arranged in a particular configuration, persons of ordinary skill in the art will appreciate that the components of the fluid analysis module 25' can be communicatively coupled and/or arranged differently than depicted in FIG. 1B without departing from the scope of the present disclosure. In addition, the example methods, apparatus, and systems described herein are not limited to a particular conveyance type but, instead, may be implemented in connection with different conveyance types including, for example, coiled tubing, wireline, wired-drill-pipe, drill string, and/or other conveyance means known in the industry.

In accordance with the present invention, the system of FIGS. 1A and 1B can be employed with the methodology of FIGS. 2A-2H to characterize the fluid properties of a petroleum reservoir of interest based upon downhole fluid analysis of samples of reservoir fluid. As will be appreciated by those skilled in the art, the surface-located electrical control system 18 and the fluid analysis module 25 of the tool 10 each include data processing functionality (e.g., one or more microprocessors, associated memory, and other hardware and/or software) that cooperate to implement the invention as described herein. The electrical control system 18 can also be realized by a distributed data processing system wherein data measured by the tool 10 is communicated in real time over a communication link (typically a satellite link) to a remote location for data analysis as described herein. The data analysis can be carried out on a workstation or other suitable data processing system (such as a computer cluster or computing grid).

The fluid analysis of FIGS. 2A-2H relies on a solubility model to characterize relative concentrations of high molecular weight fractions (resins and/or asphaltenes) as a function of depth in the oil column as related to relative solubility, density and molar volume of such high molecular weight fractions (resins and/or asphaltenes) at varying depth. In the preferred embodiment, the solubility model treats the reservoir fluid as a mixture (solution) of two parts: a solute part (resins and/or asphaltenes) and a solvent part (the lighter components other than resins and asphaltenes). The solute part is selected from a number of classes that include resins, asphaltene nanoaggregates, asphaltene clusters, and combinations thereof. For example, one class can include resins with little or no asphaltene nanoaggregates and asphaltene clusters. Another class can include asphaltene nanoaggregates with little or no resins and asphaltene clusters. A further class can include resins and asphaltene nanoaggregates with little or no asphaltene clusters. A further class can include asphaltene clusters with little or no resins and asphaltene nanoaggregates. The solvent part is a mixture whose properties are measured by downhole fluid analysis and/or estimated by the EOS model. It is assumed that the reservoir fluids are connected (i.e., there is a lack of compartmentalization) and in thermodynamic equilibrium. In this approach, the relative concentration (volume fraction) of the solute part as a function of depth is given by:

$$\frac{\phi_i(h_2)}{\phi_i(h_1)} = \exp\left\{\frac{v_i g(\rho_m - \rho_i)(h_2 - h_1)}{RT} + \left(\frac{v_i}{v_m}\right)_{h_2} - \left(\frac{v_i}{v_m}\right)_{h_1} - \frac{v_i\left[(\delta_i - \delta_m)^2_{h_2} - (\delta_i - \delta_m)^2_{h_1}\right]}{RT}\right\} \quad (1)$$

where $\phi_i(h_1)$ is the volume fraction for the solute part at depth $h_1$, $\phi_i(h_2)$ is the volume fraction for the solute part at depth $h_2$, $\upsilon_i$ is the partial molar volume for the solute part, $\upsilon_m$ is the molar volume for the solution, $\delta_i$ is the solubility parameter for the solute part, $\delta_m$ is the solubility parameter for the solution, $\rho_i$ is the partial density for the solute part, $\rho_m$ is the density for the solution, R is the universal gas constant, T is the absolute temperature of the reservoir fluid, and g is the gravitational constant.

In Eq. 1 it is assumed that properties of the solute part (resins and asphaltenes) are independent of depth. For properties of the solution that are a function of depth, average values are used between the two depths, which does not result in a loss of computational accuracy. Further, if the concentrations of resins and asphaltenes are small, the properties of the solute and solvent parts (the solution) with subscript m approximate those of the solvent part. The first exponential term of Eq. (1) arises from gravitational contributions. The second and third exponential terms arise from the combinatorial entropy change of mixing. The fourth exponential term arises from the enthalpy (solubility) change of mixing. It can be assumed that the reservoir fluid is isothermal. In this case, the temperature T can be set to the average formation temperature as determined from downhole fluid analysis. Alternatively, a temperature gradient with depth (preferably a linear temperature distribution) can be derived from downhole fluid analysis and the temperature T at a particular depth determined from such temperature gradient.

The density $\rho_m$ of the solution at a given depth can be derived from the partial densities of the components of the solution at the given depth by:

$$\rho_m = \sum_j \rho_j \phi_j \quad (2)$$

where $\phi_j$ is the volume fraction of the component j of the solution at the given depth, and $\rho_j$ is the partial density for the component j of the solution at the given depth.

The volume fractions $\phi_j$ for the components of the solution at the given depth can be measured, estimated from measured mass or mole fractions, estimated from the solution of the compositional gradients produced by the EOS model, or other suitable approach. The partial density $\rho_j$ for the components of the solution at the given depth can be known, estimated from the solution of the compositional gradients produced by the EOS model, or other suitable approach. For example, the asphaltene density can be assumed to be 1.2 g/cm³ and the solvent density can be estimated using correlations or the EOS model.

The molar volume $v_m$ for the solution at a given depth can be derived by:

$$v_m = \frac{\sum_j x_j m_j}{\rho_m} \quad (3)$$

where $x_j$ is the mole fraction of component j of the solution, $m_j$ is the molar mass of component j of the solution, and $\rho_m$ is the density of the solution.

The mole fractions $x_j$ of the components of the solution at the given depth can be measured, estimated from measured mass or mole fractions, estimated from the solution of the compositional gradients produced by the EOS model, or other suitable approach. The molar mass $m_j$ for the components of the solution are known. The density $\rho_m$ for the solution at the given depth is provided by the solution of equation (2).

The solubility parameter $\delta_m$ for the solution at a given depth can be derived as the average of the solubility parameters for the components of the solution at the given depth, given by:

$$\delta_m = \left(\sum_h \phi_j \delta_j\right) \bigg/ \sum_j \phi_j \quad (4)$$

where $\phi_j$ is the volume fraction of the component j of the solution at the given depth, and $\delta_j$ is the solubility parameter for the component j of the solution at the given depth.

The volume fraction $\phi_j$ of the components of the solution at the given depth can be measured, estimated from measured mass or mole fractions, estimated from the solution of the compositional gradients produced by the EOS model, or other suitable approach. The solubility parameters $\delta_j$ of the components of the solution at the given depth can be known, or estimated from measured mass or mole fractions, estimated from the solution of the compositional gradients produced by the EOS model, or other suitable approach.

It is also contemplated that the solubility parameter $\delta_m$ for the solution at a given depth can be derived from an empirical correlation to the density $\rho_m$ of the solution at a given depth. For example, the solubility parameter $\delta_m$ (in (MPa)$^{0.5}$) can be derived from:

$$\delta_m = D\rho_m + C \quad (5)$$

where $D = (0.004878 R_s + 9.10199)$,
$C = (8.3271 \rho_m - 0.004878 R_s \rho_m + 2.904)$,
$R_s$ is the GOR at the given depth in scf/STB, and
$\rho_m$ is the bulk live oil density at the given depth in g/cm³.

The GOR($R_s$) as a function of depth in the oil column can be measured by downhole fluid analysis or derived from the predictions of compositional components of the reservoir fluid as a function of depth as described below. The bulk live oil density ($\rho_m$) as a function of depth can be measured by downhole fluid analysis or derived from the predictions of compositional components of the reservoir fluid as a function of depth. In another example, the solubility parameter $\delta_m$ (in (MPa)$^{0.5}$) can be derived from a simple correlation to the density $\rho_m$ of the solution at a given depth (in g/cm³) given by:

$$\delta_m = 17.347 \rho_m + 2.904 \quad (6)$$

The solubility parameter $\delta_i$ of the solute part (in MPa$^{0.5}$) can be derived from a given temperature gradient relative to a reference measurement station ($\Delta T = T - T_0$) by:

$$\delta_i(T) = \delta_i(T_0)[1 - 1.07 \times 10^{-3}(\Delta T)] \quad (7)$$

where $T_0$ is the temperature at reference measurement station (e.g., $T_0 = 298.15$ K), and $\delta_i(T_0)$ is a solubility parameter $\delta_i$ of the solute part (in MPa$^{0.5}$) at $T_0$ (e.g., $\delta_i(T_0) = 20.5$ MPa$^{0.5}$ for the class where the solute part include resins (with little or no asphaltene nanoaggregates or asphaltene clusters), and $\delta_i(T_0) = 21.85$ MPa$^{0.5}$ for those classes where the solute part includes asphaltenes (such as classes that include asphaltene nanoaggregates, asphaltene clusters and asphaltene nanoaggregate/resin combinations).

The impact of pressure on the solubility parameter $\delta_i$ of the solute part is small and negligible.

The partial density $\rho_i$ for the solute part (in kg/m³) can be derived from constants, such as 1150 kg/m³ for the class where the solute part include resins (with little or no asphaltene nanoaggregates or asphaltene clusters), and 1200 kg/m³ for those classes where the solute part includes asphaltenes (such as classes that include asphaltene nanoaggregates, asphaltene clusters and asphaltene nanoaggregate/resin combinations).

Other types of functions can be employed to correlate the properties of the solute part as a function of depth. For example, a linear function of the form of Eq. (8) can be used to correlate a property of the solute part (such as partial density and solubility parameter) as a function of depth $$\alpha = c\Delta h + \alpha_{ref} \quad (8)$$

where $\alpha$ is the property (such as partial density and solubility parameter) of the solute part, c is a coefficient, $\alpha_{ref}$ is the property of the solute part at a reference depth, and $\Delta h$ is the difference in height relative to the reference depth.

Once the properties noted above are obtained, the remaining adjustable parameter in Eq. (1) is the molar volume of the solute part. The molar volume of the solute part varies for the different classes. For example, resins have a smaller molar volume than asphaltene nanoaggregates, which have a smaller molar volume than asphaltene clusters. The model assumes that the molar volume of the solute part is constant as function of depth. A spherical model is preferably used to estimate the molar volume of the solute part by:

$$V = \frac{1}{6} * \pi * d^3 * Na \qquad (9)$$

where V is the molar volume, d is the molecular diameter, and Na is Avogadro's constant.

For example, for the class where the solute part includes resins (with little or no asphaltene nanoaggregates and asphaltene clusters), the molecular diameter d can vary over a range of 1.25±0.15 nm. For the class where the solute part includes asphaltene nanoaggregates (with little or no resins and asphaltene clusters), the molecular diameter d can vary over a range of 1.8±0.2 nm. For the class where the solute part includes asphaltene clusters (with little or no resins and asphaltene nanoaggregates), the molecular diameter d can vary over a range of 4.0±0.5 nm. For the class where the solute part is a mixture of resins and asphaltene nanoaggregates (with little or no asphaltene clusters), the molecular diameter d can vary over the range corresponding to such resins and nanoaggregates (e.g., between 1.25 nm and 1.8 nm). These diameters are exemplary in nature and can be adjusted as desired.

In this manner, Eq. (1) can be used to determine a family of curves for each solute part class. The family of curves represents an estimation of the concentration of the solute part class part as a function of height. Each curve of the respective family is derived from a molecular diameter d that falls within the range of diameters for the corresponding solute part class. A solution can be solved by fitting the curves to corresponding measurements of the concentration of the respective solute part class at varying depths as derived from downhole fluid analysis to determine the best matching curve. For example, the family of curves for the solute part class including resins (with little or no asphaltene nanoaggregates and clusters) can be fit to measurements of resin concentrations at varying depth. In another example, the family of curves for the solute part class including asphaltene nanoaggregates (with little or no resins and asphaltene clusters) can be fit to measurements of asphaltene nanoaggregrate concentrations at varying depth. In still another example, the family of curves for the solute part class including asphaltene clusters (with little or no resins and asphaltene nanoaggregates) can be fit to measurements of asphaltene cluster concentrations at varying depth. In yet another example, the family of curves for the solute part class including resins and asphaltene nanoaggregates (with little or no asphaltene clusters) can be fit to measurements of mixed resins and asphaltene nanoaggregate concentrations at varying depth. If a best fit is identified, the estimated and/or measured properties of the best matching solute class (or other suitable properties) can be used for reservoir analysis. If no fit is possible, then the reservoir fluids might not be in equilibrium or a more complex formulism may be required to describe the petroleum fluid in the reservoir.

Other suitable structural models can be used to estimate and vary the molar volume for the different solute part classes. It is also possible that Eq. (1) can be simplified by ignoring the first and second exponent terms, which gives an analytical model of the form:

$$\frac{\phi_i(h_2)}{\phi_i(h_1)} = \exp\left\{\frac{v_i g (\rho_m - \rho_i)(h_2 - h_1)}{RT}\right\} \qquad (10)$$

This Eq. (10) can be solved in a manner similar to that described above for Eq. (1) in order to derive the relative concentration of solute part as a function of depth (h) in the reservoir.

The operations of FIGS. 2A-2H begin in step 201 by employing the DFA tool of FIGS. 1A and 1B to obtain a sample of the formation fluid at the reservoir pressure and temperature (a live oil sample) at a measurement station in the wellbore (for example, a reference station). The sample is processed by the fluid analysis module 25. In the preferred embodiment, the fluid analysis module 25 performs spectrophotometry measurements that measure absorption spectra of the sample and translates such spectrophotometry measurements into concentrations of several alkane components and groups in the fluids of interest. In an illustrative embodiment, the fluid analysis module 25 provides measurements of the concentrations (e.g., weight percentages) of carbon dioxide ($CO_2$), methane ($CH_4$), ethane ($C_2H_6$), the C3-C5 alkane group including propane, butane, pentane, the lump of hexane and heavier alkane components (C6+), and asphaltene content. The tool 10 also preferably provides a means to measure temperature of the fluid sample (and thus reservoir temperature at the station), pressure of the fluid sample (and thus reservoir pressure at the station), live fluid density of the fluid sample, live fluid viscosity of the fluid sample, gas-oil ratio (GOR) of the fluid sample, optical density, and possibly other fluid parameters (such as API gravity, formation volume fraction (FVF), etc.) of the fluid sample.

In step 203, a delumping process is carried out to characterize the compositional components of the sample analyzed in 301. The delumping process splits the concentration (e.g., mass fraction, which is sometimes referred to as weight fraction) of given compositional lumps (C3-C5, C6+) into concentrations (e.g., mass fractions or weight fractions) for single carbon number (SCN) components of the given compositional lump (e.g., split C3-C5 lump into C3, C4, C5, and split C6+ lump into C6, C7, C8 . . . ). Details of the exemplary delumping operations carried out as part of step 203 are described in detail in U.S. Pat. No. 7,920,970, entitled "Methods and Apparatus for Characterization of Petroleum Fluid and Applications Thereof," herein incorporated by reference in its entirety.

In step 205, the results of the delumping process of step 203 are used in conjunction with an equation of state (EOS) model to predict compositions and fluid properties (such as volumetric behavior of oil and gas mixtures) as a function of depth in the reservoir. In the preferred embodiment, the predictions of step 205 include property gradients, pressure gradients and temperature gradients of the reservoir fluid as a function of depth. The property gradients preferably include mass fractions, mole fractions, molecular weights and specific gravities for a set of SCN components (but not for asphaltenes) as a function of depth in the reservoir. The property gradients predicted in step 205 preferably do not include compositional gradients (i.e., mass fractions, mole fractions, molecular weights and specific gravities) for resin and asphaltenes as a function of depth as such analysis is provided by a solubility model as described herein in more detail.

The EOS model of step 205 includes a set of equations that represent the phase behavior of the compositional components of the reservoir fluid. Such equations can take many forms. For example, they can be any one of many cubic EOS as is well known. Such cubic EOS include van der Waals EOS (1873), Redlich-Kwong EOS (1949), Soave-Redlich Kwong EOS (1972), Peng-Robinson EOS (1976), Stryjek-Vera-Peng-Robinson EOS (1986) and Patel-Teja EOS (1982). Volume shift parameters can be employed as part of the cubic EOS in order to improve liquid density predictions as is well known. Mixing rules (such as van ser Waals mixing rule) can also be employed as part of the cubic EOS. A SAFT-type EOS can also be used as is well known in the art. In these equations, the deviation from the ideal gas law is largely accounted for by introducing (1) a finite (non-zero) molecular volume and (2) some molecular interaction. These parameters are then related to the critical constants of the different chemical components.

In the preferred embodiment, the EOS model of step 205 predicts compositional gradients with depth that take into account the impacts of gravitational forces, chemical forces, thermal diffusion, etc. To calculate compositional gradients with depth in a hydrocarbon reservoir, it is usually assumed that the reservoir fluids are connected (i.e., there is a lack of compartmentalization) and in thermodynamic equilibrium (with no adsorption phenomena or any kind of chemical reactions in the reservoir). The mass flux (J) of compositional component i that crosses the boundary of an elementary volume of the porous media is expressed as:

$$J_i = \rho_i \left( \sum_{j=1}^{n} (L_{ij} \nabla_T g_j^t) + L_{ip}(\rho g - \nabla P) + L_{iq} \nabla T \right) \quad (11)$$

where $L_{ij}$, $L_{ip}$, and $L_{iq}$ are the phenomenological coefficients, $\rho_i$ denotes the partial density of component i, $\rho$, g, P, T are the density, the acceleration, pressure, and temperature, respectively, and $g_j^t$ is the contribution of component j to mass free energy of the fluid in a porous media, which can be divided into a chemical potential part $\mu_j$ and a gravitational part gz (where z is the vertical depth).

The average fluid velocity (u) is estimated by:

$$u = \frac{\sum_{j=1}^{n} J_j}{\rho} \quad (12)$$

According to Darcy's law, the phenomenological baro-diffusion coefficients must meet the following constraint:

$$\frac{k}{\eta} = \frac{\sum_{j=1}^{n} \rho_j L_{jp}}{\rho} \quad (13)$$

where k and $\eta$ are the permeability and the viscosity, respectively.

If the pore size is far above the mean free path of molecules, the mobility of the components, due to an external pressure field, is very close to the overall mobility. The mass chemical potential is a function of mole fraction (x), pressure, and temperature.

At constant temperature, the derivative of the mass chemical potential ($\mu_j$) has two contributions:

$$\nabla_T \mu_j = \sum_{k=1}^{n} \left( \frac{\partial \mu_j}{\partial x_k} \right)_{T,P,x_{i \neq k}} \nabla x_k + \left( \frac{\partial \mu_j}{\partial P} \right)_{T,x} \nabla P \quad (14)$$

where the partial derivatives can be expressed in terms of EOS (fugacity coefficients):

$$\left( \frac{\partial \mu_j}{\partial x_k} \right)_{T,P,x_{j \neq k}} = \frac{RT}{M_j} \left( \frac{\partial \ln f_j}{\partial x_k} \right)_{T,P,x_{j \neq k}} = \frac{RT}{M_j} \left( \frac{\delta_{jk}}{x_k} + \frac{1}{\varphi_j} \left( \frac{\partial \varphi_j}{\partial x_k} \right)_{T,P,x_{j \neq k}} \right) \quad (15)$$

$$\left( \frac{\partial \mu_j}{\partial P} \right)_{T,x} = \frac{\bar{v}_j}{M_j} = \frac{RT}{M_j} \left( \frac{1}{P} + \left( \frac{\partial \varphi_j}{\partial P} \right)_{T,x} \right) \quad (16)$$

where $M_j$, $f_j$, $\phi_j$, and $v_j$ are the molecular mass, fugacity, fugacity coefficient, and partial molar volume of component j, respectively;

$x_k$ is the mole fraction of component k;

R denotes the universal gas constant; and $\delta$ is the Kronecker delta function.

In the ideal case, the phenomenological coefficients (L) can be related to effective practical diffusion coefficients ($D_i^{eff}$):

$$L_{ii} = -\frac{M_i}{RT} D_i^{eff} \quad (17)$$

The mass conservation for component i in an n-component reservoir fluid, which governs the distribution of the components in the porous media, is expressed as:

$$\frac{\partial \rho_i}{\partial t} + \nabla J_i = 0, \quad (18)$$
$$i = 1, 2, \ldots, n$$

The equation can be used to solve a wide range of problems. This is a dynamic model which is changing with time t.

Let us consider that the mechanical equilibrium of the fluid column has been achieved:

$$\nabla_z P = \rho g \quad (19)$$

The vertical distribution of the components can be calculated by solving the following set of equations:

$$\frac{\partial \ln f_i}{\partial z} - \frac{M_i g}{RT} + \frac{J_{i,z}}{x_i D_i^{eff}} \frac{M}{\rho M_i} - \frac{L_{iq}}{D_i^{eff}} \frac{\partial T}{\partial z} = 0, \quad (20)$$
$$i = 1, 2, \ldots, n$$

and $$\sum_{k=1}^{n} \left( \frac{\delta_{ik}}{x_k} + \frac{1}{\varphi_i} \frac{\partial \varphi_i}{\partial x_k} \right) \nabla_z x_k + \frac{(v_i \rho - M_i)g}{RT} + \frac{J_{i,z}}{x_i D_i^{eff}} \frac{M}{\rho M_i} - \frac{L_{iq}}{D_i^{eff}} \frac{\partial T}{\partial z} = 0 \quad (21)$$

where $J_{i,z}$ is the vertical component of the external mass flux and M is the average molecular mass, such as the average molecular mass of the charged analyte gas.

This formulation allows computation of the stationary state of the fluid column and it does not require modeling of the dynamic process leading to the observed compositional distribution.

If the horizontal components of external fluxes are significant, the equations along the other axis have to be solved as well. Along a horizontal "x" axis the equations become:

$$\frac{\partial \ln f_i}{\partial x} + \frac{J_{i,x}}{x_i D_i^{eff}} \frac{M}{\rho M_i} - \frac{L_{iq}}{D_i^{eff}} \frac{\partial T}{\partial x} = 0 \qquad (22)$$

The mechanical equilibrium of the fluid column $\nabla_z P = \rho g$, is a particular situation which will occur only in highly permeable reservoirs. In the general case, the vertical pressure gradient is calculated by:

$$\nabla_z P = \rho g - \frac{\nabla_z P_{Fluxes} + \nabla_z P_{Soret}}{1 + R_p} \qquad (23)$$

where $R_p$ is calculated by $$R_p = RT \frac{k}{\eta} \frac{\rho}{M} \sum_{i=1}^{n} \frac{x_i}{D_i^{eff}}. \qquad (24)$$

The pressure gradient contribution from thermal diffusion (so-called Soret contribution) is given by:

$$\nabla_z P_{Soret} = RT \frac{\rho}{M} \sum_{i=1}^{n} x_i \frac{L_{iq}}{D_i^{eff}} \nabla_z T. \qquad (25)$$

And the pressure gradient contribution from external fluxes is expressed as $$\nabla_z P_{Fluxes} = RT \sum_{i=1}^{n} \frac{J_{i,z}}{M_i D_i^{eff}}. \qquad (26)$$

Assuming an isothermal reservoir and ignoring the external flux, results in the following equation:

$$\frac{\partial \ln f_i}{\partial z} - \frac{M_i g}{RT} = 0, \quad i = 1, 2, \ldots, n. \qquad (27)$$

The equation (27) can be rewritten as $$\frac{\partial \ln f_i}{\partial z} - \frac{M_i g}{RT} + a_i = 0, \quad i = 1, 2, \ldots, n. \qquad (28)$$

where $a_i$ is computed by:

$$a_i = \frac{J_{i,z}}{x_i D_i^{eff}} \frac{M}{\rho M_i} - \frac{L_{iq}}{D_i^{eff}} \frac{\partial T}{\partial z}, \quad i = 1, 2, \ldots, n. \qquad (29)$$

The first part of the $a_i$ term of Eq. (29) can be simplified to $$\frac{J_{i,z}}{x_i \rho D_i^{eff}}. \qquad (30)$$

The second part of the $a_i$ term of Eq. (29) can be written in the form proposed by Haase in "Thermodynamics of Irreversible Processes," Addison-Wesley, Chapter 4, 1969. In this manner, $a_i$ is computed by:

$$a_i = \frac{J_{i,z}}{x_i \rho D_i^{eff}} + M_i \left( \frac{H_m}{M_m} - \frac{H_i}{M_i} \right) \frac{\Delta T}{T}, \quad i = 1, 2, \ldots, n \qquad (31)$$

where $H_i$ is the partial molar enthalpy for component i, $H_m$ is the molar enthalpy for the mixture, $M_i$ is the molecular mass for component i, $M_m$ is the molecular mass for the mixture, T is the formation temperature, and $\Delta T$ is the temperature difference between two depths.

The first part of the $a_i$ term of Eqs. (29) and (30) accounts for external fluxes in the reservoir fluid. It can be ignored if a steady-state is assumed. The second part of the $a_i$ term of Eqs. (29) and (31) accounts for a temperature gradient in the reservoir fluid. It can be ignored if an isothermal reservoir is assumed.

The fugacity $f_i$ of component i at a given depth can be expressed as function of the fugacity coefficient and mole fraction for the component i and reservoir pressure (P) at the given depth as $$f_i = \phi_i x_i P. \qquad (32)$$

The mole fractions of the components at a given depth must further sum to 1 such that $$\sum_{i=1}^{N} x_i = 1$$

at a given depth. Provided the mole fractions and the reservoir pressure and temperature are known at the reference station, these equations can be solved for mole fractions (as well as mass fractions), partial molar volumes and volume fractions for the reservoir fluid components as well as pressure and temperature as a function of depth. Flash calculations can solve for fugacities of components of the reservoir fluid that form at equilibrium. Details of suitable flash calculations are described by Li in "Rapid Flash Calculations for Compositional Simulation," SPE Reservoir Evaluation and Engineering, October 2006, herein incorporated by reference in its entirety. The flash equations are based on a fluid phase equilibria model that finds the number of phases and the distribution of species among the phases, that minimizes Gibbs Free Energy. More specifically, the flash calculations calculate the equilibrium phase conditions of a mixture as a function of pressure, temperature and composition.

In step 205, the predictions of compositional gradient can be used to predict properties of the reservoir fluid as a function of depth (typically referred to as a property gradient) as is well known. For example, the predictions of compositional gradient can be used to predict bulk fluid properties (such as molar volume, molecular weight, live fluid density, stock tank density, bubble point pressure, dew point pressure, gas-oil ratio, live fluid density) as well as other pressure-volume-temperature (PVT) properties of the reservoir fluid as a function of depth in the reservoir. The EOS of step 205 preferably calculates the predictions of compositional gradient without taking into account resins and asphaltenes separately and specially as such predictions are provided by a solubility model as described herein in more detail.

In step 207, the DFA tool 10 of FIGS. 1A and 1B is used to obtain a sample of the formation fluid at the reservoir pressure and temperature (a live oil sample) at another measurement station in the wellbore, and the downhole fluid analysis as described above with respect to step 201 is performed on this sample. In an illustrative embodiment, the fluid analysis module 25 provides measurements of the concentrations (e.g., weight percentages) of carbon dioxide ($CO_2$), methane ($CH_4$), ethane ($C_2H_6$), the C3-C5 alkane group including propane, butane, pentane, the lump of hexane and heavier alkane components (C6+), and asphaltene content. The tool 10 also preferably provides a means to measure temperature of the fluid sample (and thus reservoir temperature at the station), pressure of the fluid sample (and thus reservoir pressure at the station), live fluid density of the fluid sample, live fluid viscosity of the fluid sample, gas-oil ratio (GOR) of the fluid sample, optical density, and possibly other fluid parameters (such as API gravity, formation volume fraction (FVF), etc.) of the fluid sample.

Optionally, in step 209 the EOS model of step 205 can be tuned based on a comparison of the compositional and fluid property predictions derived by the EOS model of step 205 and the compositional and fluid property analysis of the DFA tool in 207. Laboratory data can also be used to tune the EOS model. Such tuning typically involves selecting parameters of the EOS model in order to improve the accuracy of the predictions generated by the EOS model. EOS model parameters that can be tuned include critical pressure, critical temperature and a centric factor for single carbon components, binary interaction coefficients, and volume translation parameters. An example of EOS model tuning is described in Reyadh A. Almehaideb et al., "EOS tuning to model full field crude oil properties using multiple well fluid PVT analysis," Journal of Petroleum Science and Engineering, Volume 26, Issues 1-4, pgs. 291-300, 2000, herein incorporated by reference in its entirety. In the event that the EOS model is tuned, the compositional and fluid property predictions of step 205 can be recalculated from the tuned EOS model.

In step 211, the predictions of compositional gradients generated in step 205 (or in step 209 in the event that EOS is tuned) are used to derive solubility parameters of the solvent part (and possibly other property gradients or solubility model inputs) as a function of depth in the oil column. For example, the predictions of compositional gradients can be used to derive the density of the solvent part (Eq. (2)), the molar volume of the solvent part (Eq. (3)), and the solubility parameter of the solvent part (Eq. (4) or (5)) as a function of depth.

In steps 213 to 219, the solute part is treated as a particular first-type class, for example a class where the solute part includes resins (with little or no asphaltene nanoaggregates and asphaltene clusters). This class generally corresponds to reservoir fluids that include condensates with very small concentration of asphaltenes. Essentially, the high content of dissolved gas and light hydrocarbons create a poor solvent for asphaltenes. Moreover, the processes that generate condensates do not tend to generate asphaltenes. For this class, the operations rely on an estimate that the average spherical diameter of resins is 1.25±0.15 nm and that resins impart color at a predetermined visible wavelength (647 nm). The average spherical diameter of 1.25±0.15 nm corresponds to an average molecular weight of 740±250 g/mol. Laboratory centrifuge data also has shown the spherical diameter of resins is ~1.3 nm. This is consistent with the results in the literature. It is believed that resins impart color in the shorter visible wavelength range due to their relatively small number of fused aromatic rings ("FARs") in polycyclic aromatic hydrocarbons ("PAHs"). In contrast, asphaltenes impart color in both the short visible wavelength range and the longer near-infrared wavelength range due to their relatively larger number of FARs in PAHs. Consequently, resins and asphaltenes impart color in the same visible wavelength range due to overlapping electronic transitions of the numerous PAHs in the oil. However, in the longer near-infrared wavelength range, the optical absorption is predominantly due to asphaltenes.

In step 215, a number of average spherical diameter values within the range of 1.25±0.15 nm (e.g., d=1.1 nm, d=1.2 nm, d=1.3 nm and d=1.4 nm) are used to estimate corresponding molar volumes for the particular solute part class utilizing Eqn. (9).

In step 217, the molar volumes estimated in step 215 are used in conjunction with the Flory-Huggins-Zuo type solubility model described above with respect to Eqn. (1) to generate a family of curves that predict the concentration of the particular solute part class of step 213 as a function of depth in the reservoir.

In step 219, the family of curves generated in step 217 is compared to measurement of resin concentration at corresponding depths as derived from associated DFA color measurements at the predetermined visible wavelength (647 nm). The comparisons are evaluated to identify the diameter that best satisfies a predetermined matching criterion. In the preferred embodiment, the matching criterion determines that there are small differences between the resin concentrations as a function of depth as predicted by the Flory-Huggins-Zuo type solubility model and the corresponding resin concentrations measured from DFA analysis, thus providing an indication of a proper match within an acceptable tolerance level.

In steps 221 to 227, the solute part is treated as a particular second-type class, for example a class where the solute part includes asphaltene nanoaggregates (with little or no resins and asphaltene clusters). This class generally corresponds to low GOR black oils that usually have little compressibility. These types of black oils often contain asphaltene molecules with 4 to 7 FARs in PAHs. The asphaltene molecules are dispersed in the oil as nanoaggregates with an aggregation number of 2-8. For this class, the operations rely on an estimate that the average spherical diameter of asphaltene nanoaggregates is 1.8±0.2 nm and that the asphaltene nanoaggregates impart color at a predetermined NIR wavelength (1070 nm). The average spherical diameter of 1.8±0.2 nm corresponds to an average molecular weight of 2200±700 g/mol. This is consistent with the results in the literature. Field and laboratory analysis have shown that asphaltene nanoaggregates impart color in both the visible wavelength range around 640 nm and the near wavelength range around 1070 nm. It is believed that the asphaltene nanoaggregates impart color in both the short visible wavelength range and the longer near-infrared wavelength range due to their relatively larger number of FARs in PAHs.

In step 223, a number of average spherical diameter values within the range of 1.8±0.2 nm (e.g., d=1.6 nm, d=1.7 nm, d=1.8 nm, d=1.9 and d=2.0 nm) are used to estimate corresponding molar volumes for the particular solute part class utilizing Eqn. (9).

In step 225, the molar volumes estimated in step 223 are used in conjunction with the Flory-Huggins-Zuo type solubility model described above with respect to Eqn. (1) to generate a family of curves that predict the concentration of the particular solute part class of step 221 as a function of depth in the reservoir.

In step 227, the family of curves generated in step 225 is compared to measurement of asphaltene nanoaggregate concentration at corresponding depths as derived from associated DFA color measurements at the predetermined NIR wavelength (1070 nm). The comparisons are evaluated to identify the diameter that best satisfies a predetermined matching criterion. In the preferred embodiment, the matching criterion determines that there are small differences between the asphaltene nanoaggregate concentrations as a function of depth as predicted by the Flory-Huggins-Zuo type model and the corresponding asphaltene nanoaggregate concentrations measured from DFA analysis, thus providing an indication of a proper match within an acceptable tolerance level.

In steps 229 to 235, the solute part is treated as a particular third-type class, for example a class where the solute part includes a combination of resins and asphaltene nanoaggregates (with little or no asphaltene clusters). This class generally corresponds to black oils that include a mixture of resins and asphaltene nanoaggregates. For this class, the operations rely on an estimate that the average spherical diameter of the mixed resins and asphaltene nanoaggregates varies linearly from 1.5±0.2 nm to 2.0±0.2 nm according to wavelength in a range between a visible wavelength (647 nm) and a NIR wavelength (1070 nm). This conforms to an assumption that the average molecular diameter for mixed resin and asphaltene nanoaggregates increases linearly with increasing wavelength due to the increases importance of absorption from the asphaltene aggregates in the longer wavelength region. It is believed that the asphaltene nanoaggregate content (weight %) contributing to color increases exponentially with increasing wavelength. In the preferred embodiment, the relationship between the average spherical diameter (d) and wavelength can be given by:

$$d = C1 * \text{Wavelength} + C2 \quad (33)$$

where C1 and C2 are two constants.
C1 and C2 can be determined by solving the relation utilizing two diameter/wavelength combinations. For instance, a combination of d=1.5 nm at 647 nm and a combination of d=2.0 nm at 1070 nm can be used to solve for C1 and C2. In another example, a combination of d=1.3 nm at 647 nm and a combination of d=1.8 nm at 1070 nm can be used to solve for C1 and C2. In yet another example, a combination of d=1.7 nm at 647 nm and a combination of d=2.2 nm at 1070 nm can be used to solve for C1 and C2.

In step 231, a number of average spherical diameter values and wavelength combinations defined by the relationship of 229 are used to estimate corresponding molar volumes for the particular solute part class utilizing Eqn. (9).

In step 233, the molar volumes estimated in step 231 are used in conjunction with the Flory-Huggins-Zuo type solubility model described above with respect to Eqn. (1) to generate a family of curves that predict the concentration of the particular solute part class of step 229 as a function of depth in the reservoir. Each curve is associated with a particular average spherical diameter value and wavelength combination.

In step 235, the family of curves generated in step 233 are compared to measurement of mixed resins and asphaltene nanoaggregate concentrations at corresponding depths as derived from associated DFA color measurements at the wavelength of the given diameter/wavelength combination for the respective curve. The comparisons are evaluated to identify the diameter that best satisfies a predetermined matching criterion. In the preferred embodiment, the matching criterion determines that there are small differences between the mixed resin and asphaltene nanoaggregate concentrations as a function of depth as predicted by the Flory-Huggins-Zuo type solubility model and the corresponding mixed resin and asphaltene nanoaggregate concentrations measured from DFA analysis, thus providing an indication of a proper match within an acceptable tolerance level.

In steps 237 to 243, the solute part is treated as a particular fourth-type class, for example a class where the solute part includes asphaltene clusters. This class generally corresponds to black oils where the asphaltene gradient is very large in the oil column. This behavior implies that both asphaltene nanoaggregates and asphaltene clusters are suspended in the oil column. For this class, the operations rely on an estimate that the average spherical diameter of asphaltene clusters is 4.5±0.5 nm at a predetermined NIR wavelength (1070 nm). Field and laboratory analysis have shown that asphaltene clusters impart color in both the visible wavelength range around 640 nm and the near wavelength range around 1070 nm. It is believed that the asphaltene clusters impart color in both the short visible wavelength range and the longer near-infrared wavelength range due to their relatively larger number of FARs in PAHs.

In step 239, a number of average spherical diameter values within the range of 4.5±0.5 nm (e.g., d=4.0 nm, d=4.3 nm, d=4.5 nm, d=4.8 nm and d=5.0 nm) are used to estimate corresponding molar volumes for the particular solute part class utilizing Eqn. (9).

In step 241, the molar volumes estimated in step 239 are used in conjunction with the Flory-Huggins-Zuo type solubility model described above with respect to Eqn. (1) to generate a family of curves that predict the concentration of the particular solute part class of step 237 as a function of depth in the reservoir.

In step 243, the family of curves generated in step 241 is compared to measurement of asphaltene cluster concentration at corresponding depths as derived from associated DFA color measurements at the predetermined NIR wavelength (1070 nm). The comparisons are evaluated to identify the diameter that best satisfies a predetermined matching criterion. In the preferred embodiment, the matching criterion determines that there are small differences between the asphaltene cluster concentrations as a function of depth as predicted by the Flory-Huggins-Zuo type model and the corresponding asphaltene cluster concentrations measured from DFA analysis, thus providing an indication of a proper match within an acceptable tolerance level.

In step 245, the matching diameters identified in steps 219, 227, 235 and 243 (if any) are evaluated to determine the best matching diameter of the group. The evaluation provides an indication of which particular solute part class (and thus the assumption of composition underlying the particular solute part class) is the best match to the measured gradient for the solvent part high molecular weight fractions.

In step 247, a curve belonging to the curves generated in steps 217, 225, 233, 241 is selected that corresponds to the particular solute part class and best matching diameter identified in step 245.

In step 249, the curve selected in step 247 is used to derive concentration of the best matching solute part class as function of depth in the reservoir.

In step 251, the best matching solute part class identified in step 245 is evaluated to determine if it includes predetermined asphaltene components (such as asphaltene nanoaggregates and/or asphaltene clusters). For example, such evaluation can process a class identifier of the best matching solute part class to determine if the class identifier corresponds to a solute part class (such as the second, third and fourth type classes of steps 221, 229, and 237) that includes asphaltene nanoaggregates and/or asphaltene clusters. If so, the operations continue to step 253. Otherwise, the operations continue to step 259.

In step 253, the workflow evaluates the phase stability of the asphaltenes of the best matching solute part at multiple depths in the oil column using equilibrium criteria that involve two phases (a maltene or oil rich phase and an asphaltene rich phase) of respective components of the reservoir fluid. The equilibrium criteria for the respective components are evaluated for each component at a given depth in the oil column to determine whether or not the phase of the asphaltenes of the best matching solute part class is stable at the given depth of the oil column. If the phase of the asphaltenes of the best matching solute part class is unstable, the asphaltenes are no longer in a stable colloid and precipitate out of the reservoir fluid to form tar. Such detection can identify issues of tar formation that can lead to reservoir compartmentalization and hinder production. The evaluation of the phase of asphaltenes can be carried out over multiple depths of the reservoir to identify locations or intervals where tar formation is likely.

In a preferred embodiment, the equilibrium criteria of step 253 have the form:

$$x_i^{oil}\gamma_i^{oil} = x_i^{asph}\gamma_i^{asph} \quad (34)$$

where the subscript i corresponds to the respective component of the reservoir fluid at the given depth,
superscripts oil and asph correspond to the oil rich phase and asphaltene rich phase, respectively, of the component i at the given depth,
$x_i^{oil}$ is the mole fraction of the oil rich phase of component i of the reservoir fluid at the given depth,
$\gamma_i^{oil}$ is the activity coefficient of the oil rich phase of component i of the reservoir fluid at the given depth,
$x_i^{asph}$ is the mole fraction of the asphaltene rich phase of component i of the reservoir fluid at the given depth, and
$\gamma_i^{asph}$ is the activity coefficient of the asphaltene rich phase of component i of the reservoir fluid at the given depth.

Eqn. (34) can be rewritten to give the equilibrium ratio or the K-value of component i as:

$$K_i = x_i^{asph}/x_i^{oil} = \gamma_i^{oil}/\gamma_i^{asph}. \quad (35)$$

On the basis of one mole, the sum of the oil rich phase fraction (labeled L as it can be treated as a liquid) and the asphaltene rich phase fraction (labeled S as it can be treated as a solid or pseudo-liquid) is 1 to give:

$$L + S = 1. \quad (36)$$

A material balance for component i gives:

$$z_i = Lx_i^{oil} + Sx_i^{asph} \quad (37)$$

where $z_i$ is the mole fraction of the mixture of the oil rich phase and asphaltene rich phase of component i at the given depth.

Substituting Eqns. (35) and (36) into Eqn. (37) gives:

$$z_i = Lx_i^{oil} + (1-L)x_i^{asph} = Lx_i^{oil} + (1-L)K_i x_i^{oil} = (L + (1-L)K_i)x_i^{oil}. \quad (38)$$

Solving Eqn. (38) for $x_i^{oil}$ gives:

$$x_i^{oil} = \frac{z_i}{(L + (1-L)K_i)}. \quad (39)$$

Similarly, eqn. (38) can be rewritten to solve for $x_i^{asph}$:

$$z_i = Lx_i^{oil} + (1-L)x_i^{asph} = L\left(\frac{x_i^{asph}}{K_i}\right) + (1-L)x_i^{asph} = \left(\frac{L}{K_i} + (1-L)\right)x_i^{asph}. \quad (40)$$

Solving Eqn. (40) for $x_i^{asph}$ gives:

$$x_i^{asph} = \frac{z_i}{\left(\frac{L}{K_i} + (1-L)\right)} = \frac{K_i z_i}{(L + (1-L)K_i)}. \quad (41)$$

The oil rich phase and asphaltene rich phase mole fractions for the components are constrained by the following equation:

$$\sum_{i=1}^{N} x_i^{asph} = \sum_{i=1}^{N} x_i^{oil} = 1. \quad (42)$$

Writing Eqn. (42) in function form gives:

$$\sum_{i=1}^{N} x_i^{asph} - \sum_{i=1}^{N} x_i^{oil} = \sum_{i=1}^{N} \frac{(K_i - 1)}{(L + (1-L)K_i)} z_i = 0. \quad (43)$$

Eqns. (39), (41) and (42) define a set of non-linear equations that can be solved for the oil rich phase mole fraction $x_i^{oil}$ and the asphaltene rich phase mole fraction $x_i^{asph}$ of the components of the reservoir fluid at the given depth by iteration. Such iteration typically involves making an initial guess of the equilibrium constants $K_i$ for the N components and solving Eqn. (43) for the oil rich phase mole fraction L. For example, initially, a small amount of asphaltene may be assumed to be in the oil rich phase and a small amount of oil may be assumed to be in the asphaltene rich phase. Accordingly, in certain embodiments, the equilibrium constant $K_i$ for asphaltene may be initially set to $10^3$ and the equilibrium constant $K_i$ for the solvent may be initially set to $10^{-2}$. The solution of the oil rich phase mole fraction L with the initial equilibrium constants $K_i$ and mole fractions $z_i$ at the given depth (which is known from the results of the EOS model of step 205 or 209) are plugged into Eqns. (39) and (41) to derive the mole fractions $x_i^{oil}$ and $x_i^{asph}$ of the N components of the reservoir fluid at the given depth.

The calculated oil rich phase mole fractions $x_i^{oil}$ for the components of the reservoir fluid are used as inputs to a Flory-Huggins-Zuo type solubility model that solves for the activity coefficient $\gamma_i^{oil}$ of the oil rich phase of component i of the reservoir fluid at the given depth by:

$$\ln\gamma_i^{oil} = \ln\left(\frac{\phi_i^{oil}}{x_i^{oil}}\right) + 1 - \frac{v_i^{oil}}{v^{oil}} + \frac{v_i^{oil}}{RT}(\delta_i^{oil} - \delta^{oil})^2, \quad (44)$$

where $\phi_i^{oil}$ is the volume fraction of the oil rich phase of component i at the given depth,
$v_i^{oil}$ is the partial molar volume of the oil rich phase of component i at the given depth, $v_{oil}$ is the molar volume for the oil rich phase for all components at the given depth, $\delta_i^{oil}$ is the solubility parameter for the oil rich phase of component i at the given depth, $\delta_{oil}$ is the solubility parameter for the oil rich phase of all components at the given depth, R is the universal gas constant, and T is the absolute temperature of the reservoir fluid at the given depth.

The volume fraction $\phi_i^{oil}$ of the oil rich phase of component i at the given depth can be derived from the $x_i^{oil}$ determined using Eqns. (39), (41), and (42), as described previously. The partial molar volume $v_i^{oil}$ of the oil rich phase of component i at the given depth can be derived from the output of the EOS model, or other suitable method. The solubility parameter $\delta_i^{oil}$ of the oil rich phase of component i at the given depth can be derived from the output of the EOS model, or other suitable method, such as employing a simple correlation between density and the solubility parameter. The molar volume $v^{oil}$ for the oil rich phase for all components at the given depth is given by:

$$v_{oil} = \sum_{i=1}^{N} x_i^{oil} v_i^{oil}. \quad (45)$$

The solubility parameter $\delta_{oil}$ for the oil rich phase for all components at the given depth is given by:

$$\delta_{oil} = \sum_{i=1}^{N} \phi_i^{oil} \delta_i^{oil}. \quad (46)$$

Similarly, the calculated asphaltene mole fractions $x_i^{asph}$ for the components of the reservoir fluids are used as inputs to a Flory-Huggins-Zuo type solubility model that solves for the activity coefficient $\gamma_i^{asph}$ of the asphaltene rich phase of component i of the reservoir fluid at the given depth by:

$$\ln \gamma_i^{asph} = \ln\left(\frac{\phi_i^{asph}}{x_i^{asph}}\right) + 1 - \frac{v_i^{asph}}{v^{asph}} + \frac{v_i^{asph}}{RT}(\delta_i^{asph} - \delta^{asph})^2, \quad (47)$$

where $\phi_i^{asph}$ is the volume fraction of the asphaltene rich phase of component i at the given depth, $v_i^{asph}$ is the partial molar volume of the asphaltene rich phase of component i at the given depth, $v_{asph}$ is the molar volume for the asphaltene rich phase for all components at the given depth, $\delta_i^{asph}$ is the solubility parameter for the asphaltene rich phase of component i at the given depth, $\delta_{asph}$ is the solubility parameter for the asphaltene rich phase of all components at the given depth, R is the universal gas constant, and T is the absolute temperature of the reservoir fluid at the given depth.

The volume fraction $\phi_i^{asph}$ of the asphaltene rich phase of component i at the given depth can be derived from the $x_i^{asph}$ determined using Eqns. (39), (41), and (42), as described previously. The partial molar volume $v_i^{asph}$ of the asphaltene rich phase of component i at the given depth can be derived using downhole fluid analysis optical density (OD) fitting. The solubility parameter $\delta_i^{asph}$ of the asphaltene rich phase of component i at the given depth can be derived from the correlation described above with respect to Eqn. (7). The molar volume $v_{asph}$ for the asphaltene rich phase for all components at the given depth is given by:

$$v_{asph} = \sum_{i=1}^{N} x_i^{asph} v_i^{asph}. \quad (48)$$

The solubility parameter $\delta_{asph}$ for the asphaltene rich phase for all components at the given depth is given by:

$$\delta_{asph} = \sum_{i=1}^{N} \phi_i^{asph} \delta_i^{asph}. \quad (49)$$

The activity coefficient $\gamma_i^{oil}$ of the oil rich phase of component i provided by the solution of Eqn. (44) and the activity coefficient $\gamma_i^{asph}$ of the asphaltene rich phase of component i provided by the solution of Eqn. (47) can be used to calculate equilibrium constants $K_i$ for the N components at the given depth according to Eqn. (35) and the process repeats for additional iterations in an attempt to reach convergence. If there is not convergence, the equilibrium criteria of step 253 are unsatisfied and the stability check of step 253 passes, which provides an indication that the phase of the asphaltenes of the best matching solute part class is stable at the given depth of the oil column. If there is convergence, the equilibrium criteria of step 253 are satisfied and the stability check of step 253 fails, which provides an indication that the phase of the asphaltenes of the best matching solute part class is unstable at the given depth of the oil column. In this case, the destabilized asphaltenes precipitate out of the reservoir fluid and form tar. Such detection can identify issues of tar formation that leads to reservoir compartmentalization and hinders production.

In step 255, the result of the stability check of step 253 is evaluated to determine if it has passed or failed. If it failed, the operations continue to step 257. If it passed, the operations continue to step 259.

In step 257, the workflow declares that the asphaltenes of the best matching solute part class are not stable in the oil column and the operations continue to step 283. In step 257, data defining the location(s) (e.g., depth(s)) or intervals of the reservoir where the asphaltenes are unstable and form tar can be generated and stored and output to the user. Additional sampling and analysis of the oil column of the reservoir can be recommended (and performed) as part of step 257 to confirm the phase instability of asphaltenes and possible implications of such instability during production. The additional sampling and analysis can include the following:

collection of core samples where asphaltenes might be destabilized to ascertain whether solid asphaltenes are in the core samples; this is important because it is a reservoir quality issue and because tar formation and asphaltenes are not well understood.

collection of live oil samples for downhole fluid analysis and to check for onset pressure of asphaltene precipitation; such analysis is described in U.S. Pat. No. 6,501,072, entitled "Methods and Apparatus for Determining Precipitation Onset Pressure of Asphaltenes," commonly assigned to assignee of the present application and herein incorporated by reference in its entirety.

collection of core samples and/or live oil samples for geochemistry analysis to ascertain whether a late stage of gas charging occurred in the reservoir.

collection of core samples and/or live oils samples for analysis to confirm the implication of potential flow assurance problems during production.

collection of core samples and/or live oil samples for analysis to confirm the implication of a significant viscosity increase.

In step 259, the best matching solute part class identified in step 245 is evaluated to determine if it corresponds to the first-type solute part class of steps 213 to 219 where the solute part includes resins (with little or no asphaltene nanoaggregates and asphaltene clusters). If this condition is true, the operations continue to step 261. Otherwise the operations continue to step 263.

In step 261, the workflow declares that that the reservoir fluids are in thermal equilibrium within a non-compartmentalized reservoir, and the reservoir fluids include resins (with little or none asphaltene nanoaggregates or asphaltene clusters) in accordance with assumptions underlying the first-type solute part class of steps 213 to 219. In this case, the reservoir fluid includes condensates with a very small concentration of asphaltenes. Essentially, the high content of dissolved gas and light hydrocarbons create a very poor solvent for asphaltenes. Moreover, processes that generate condensates do not tend to generate asphaltenes. Consequently, there is very little crude oil color as determined by DFA in the near infrared. Nevertheless, there are asphaltene like molecules—the resins—that absorb visible light and at times even some near infrared light. These resin molecules are largely dispersed in the condensate as molecules—thereby reducing the impact of the gravitational term. In addition, condensates exhibit considerable gradients. Since condensates are compressible, therefore, the hydrostatic head pressure of the condensate column generates a density gradient in the column. The density gradient creates the driving force to create a chemical composition gradient. The lower density components tend to rise in the column while the higher density components tend to settle down in the column. This GOR gradient gives rise to a large solubility contrast for the resins thereby producing significant DFA color gradients. These gradients are useful to check for reservoir connectivity. Accordingly, the GOR gradient as determined by DFA analysis can be evaluated for reservoir analysis as part of step 261. The predicted and/or measured concentration of the resin component as a function of depth can also be evaluated for reservoir analysis as part of step 261. More specifically, the declaration of connectivity (non-compartmentalization) can be indicated by moderately decreasing GOR values with depth, a continuous increase of resin content as a function of depth, and/or a continuous increase of fluid density and/or fluid viscosity as a function of depth. On the other hand, compartmentalization and/or non-equilibrium can be indicated by discontinuous GOR (or if lower GOR is found higher in the column), discontinuous resin content (or if higher asphaltene content is found higher in the column), and/or discontinuous fluid density and/or fluid viscosity (or if higher fluid density and/or fluid viscosity is found higher in the column). The operations then continue to step 283.

In step 263, the best matching solute part class identified in step 245 is evaluated to determine if it corresponds to the second-type solute part class of steps 221 to 227 where the solute part includes asphaltene nanoaggregates (with little or no resins and asphaltene clusters). If this condition is true, the operations continue to step 265. Otherwise the operations continue to step 267.

In step 265, the workflow declares that that the reservoir fluids are in thermal equilibrium within a non-compartmentalized reservoir, and the reservoir fluids include asphaltene nanoaggregates (with little or no resins and asphaltene clusters) in accordance with in accordance with assumptions underlying the second-type solute part class of steps 221 to 227 where the solute part includes asphaltene nanoaggregates (with little or no resins and asphaltene clusters). In this case, the predicted and/or measured concentration of the asphaltene nanoaggregates as a function of depth can be evaluated for reservoir analysis as part of step 265. More specifically, the declaration of connectivity (non-compartmentalization) can be indicated by a continuous increase of asphaltene nanoaggregate content as a function of depth, and/or a continuous increase of fluid density and/or fluid viscosity as a function of depth. On the other hand, compartmentalization and/or non-equilibrium can be indicated by discontinuous asphaltene nanoaggregate content (or if higher asphaltene nanoaggregate content is found higher in the column), and/or discontinuous fluid density and/or fluid viscosity (or if higher fluid density and/or fluid viscosity is found higher in the column). The operations then continue to step 283.

In step 267, the best matching solute part class identified in step 245 is evaluated to determine if it corresponds to the third-type solute part class of steps 229 to 235 where the solute part includes a mix of resins and asphaltene nanoaggregates (with little or no asphaltene clusters). If this condition is true, the operations continue to step 269. Otherwise the operations continue to step 271.

In step 269, the workflow declares that that the reservoir fluids are in thermal equilibrium within a non-compartmentalized reservoir, and the reservoir fluids include a mix of resins and asphaltene nanoaggregates (with little or no asphaltene clusters) in accordance with in accordance with assumptions underlying the third-type solute part class of steps 229 to 235 where the solute part includes a mix of resins and asphaltene nanoaggregates (with little or no asphaltene clusters). In this case, the predicted and/or measured concentration of the mixture of resins and asphaltene nanoaggregates as a function of depth can be evaluated for reservoir analysis as part of step 269. More specifically, the declaration of connectivity (non-compartmentalization) can be indicated by a continuous increase of the concentration of the resin/asphaltene nanoaggregate mixture as a function of depth, and/or a continuous increase of fluid density and/or fluid viscosity as a function of depth. On the other hand, compartmentalization and/or non-equilibrium can be indicated by discontinuous concentration of the resin/asphaltene nanoaggregate mixture (or if a higher concentration of the resin/asphaltene nanoaggregate mixture is found higher in the column), and/or discontinuous fluid density and/or fluid viscosity (or if higher fluid density and/or fluid viscosity is found higher in the column). The operations then continue to step 283.

In step 271, the best matching solute part class identified in step 245 is evaluated to determine if it corresponds to the fourth-type solute part class of steps 237 to 243 where the solute part includes asphaltene clusters. If this condition is true, the operations continue to step 273. Otherwise the operations continue to step 275.

In step 273, the workflow declares that that the reservoir fluids include asphaltene clusters in accordance with in accordance with assumptions underlying the fourth-type solute part class of steps 237 to 243 where the solute part includes asphaltene clusters. In this case, the predicted and/or measured concentration of the asphaltene clusters as a function of depth can be evaluated for reservoir analysis as part of step 273. More specifically, the declaration of connectivity (non-compartmentalization) can be indicated by a continuous increase of asphaltene cluster content as a function of depth, and/or a continuous increase of fluid density and/or fluid viscosity as a function of depth. On the other hand, compartmentalization and/or non-equilibrium can be indicated by discontinuous asphaltene cluster content (or if higher asphaltene cluster content is found higher in the column), and/or discontinuous fluid density and/or fluid viscosity (or if higher fluid density and/or fluid viscosity is found higher in the column).

Note that in step 273, the asphaltene clusters are dispersed in stable condition in the oil column as dictated by the underlying determination of the phase stability of asphaltenes in the stability check of step 253. In this case, heavy oil or bitumen is expected in the oil column. Moreover, because asphaltene clusters are expected in the oil column, it is anticipated that a large density and viscosity gradients exist in the oil column, and a large API gravity increase exists in the oil column. In the case of step 273, simple viscosity models can be used to characterize the viscosity of the heavy oil column.

For example, a viscosity model developed by Pal and Rhodes can be used to characterize viscosity of the heavy oil column in step 273. The Pal and Rhodes viscosity model is described in Pal, R., and Rhodes, E., "Viscosity/concentration relationships for emulsions," Journal of Rheology, Vol. 33, 1989, pgs. 1021-1045. The Pal and Rhodes viscosity model takes into account the solvation impact of a concentrated emulsion. In the Pal-Rhodes viscosity model, the emulsion droplets are assumed to be spherical. Lin et al. "Asphaltenes: fundamentals and applications: The effects of asphaltenes on the chemical and physical characteristics of asphalt." Shu, E Y, and Mullins, O, C., editors, New York, Plenum Press, 1995, pp. 155-176, modified the Pal-Rhodes viscosity model to account for non-spherical dispersed solid particles in a suspension as follows:

$$\frac{\eta}{\eta_M} = [1 - K \cdot \phi]^{-\nu} \qquad (50)$$

where $\eta$ and $\eta_M$ are the viscosity of a colloidal solution and the continuous phase (solvent), respectively;

K is the solvation constant;

$\phi$ is the volume fraction of the dispersed phase (i.e., asphaltenes); and $\nu$ is the shape factor ($\nu=2.5$ for rigid spherical particles in the original Pal-Rhodes model, and $\nu=6.9$ for heavy oil as set forth in Lin et al.).

The asphaltene (cluster) volume fraction $\phi$ can be expressed as a function of asphaltene (cluster) weight fraction at a given depth as follows:

$$\phi = \frac{\rho}{\rho_a} A, \qquad (51)$$

where $\rho$ and $\rho_a$ are the densities of oil mixtures and asphaltenes (clusters), respectively, at the given depth, and A is the weight fraction of asphaltenes (clusters) at the given depth.

Substituting Eqn. (51) into (50) gives:

$$\frac{\eta}{\eta_M} = [1 - K' \cdot A]^{-\nu}, \qquad (52)$$

where K' is a solvation constant (different from K) represented by $$\frac{\rho}{\rho_a} K.$$

If viscosity at a reference location ($\eta_0$) is known, the Pal-Rhodes viscosity model can be used to calculate the viscosity $\eta$ of the heavy oil at stock tank conditions as follows:

$$\frac{\eta}{\eta_0} = \left[\frac{1 - K' \cdot A}{1 - K' \cdot A_0}\right]^{-\nu}, \qquad (53)$$

where the subscript 0 denotes the properties at the reference location.

The weight fraction of asphaltenes A and $A_0$ can be derived from optical density fitting and the correlation between optical density and asphaltene content. K' is calculated from the expression $$K' = \frac{\rho}{\rho_a} K,$$

where the density $\rho$ can be derived from the following:

$$\frac{1}{\rho} = \frac{A}{\rho_a} + \frac{(1-A)}{\rho_M}, \qquad (54)$$

where $\rho_a$ is the density of asphaltene (=1.2 g/cc), and $\rho_M$ is the density of maltenes.

The density of maltenes $\rho_m$ can be treated as an adjustable parameter and derived from the EOS model.

In another example, a viscosity model developed by Mooney can be used to characterize viscosity of the heavy oil column in step 273. The Mooney viscosity model for heavy oil is described in Mooney, "The viscosity of a concentrated suspension of spherical particles," J. Colloid Science, Vol. 6, 1951, pgs. 162-170 as follows:

$$\frac{\eta}{\eta_M} = \exp\left[\frac{[\eta]\phi}{1 - \frac{\phi}{\phi_{max}}}\right], \qquad (55)$$

where $\eta$ and $\eta_M$ are the viscosity of a colloidal solution and the continuous phase (solvent), respectively;

$[\eta]$ is the intrinsic viscosity;

$\phi$ is the volume fraction of the dispersed phase; and $\phi_{max}$ is the packing volume fraction.

The Mooney viscosity model can be modified for heavy oil as follows:

$$\frac{\eta}{\eta_M} = \exp\left[\frac{[\eta]A}{1 - \frac{A}{A_{max}}}\right] \quad (56)$$

where A is the weight fraction of asphaltenes; and $A_{max}$ is a parameter, which can be set to 0.7.

If the viscosity at a reference location ($\eta_0$) is known, the Mooney viscosity model can be used to calculate the viscosity $\eta$ of the heavy oil at stock tank conditions as follows:

$$\frac{\eta}{\eta_M} = \exp\left[[\eta]\left(\frac{A}{1-\frac{A}{A_{max}}} - \frac{A_0}{1-\frac{A_0}{A_{max}}}\right)\right]. \quad (57)$$

The subscript 0 denotes the properties at the reference location. The weight fraction of asphaltenes A and $A_0$ can be derived from optical density fitting and the correlation between optical density and asphaltene content. The intrinsic viscosity $[\eta]$ can be treated as an adjustable parameter.

The viscosity models as described above can be extended to account for the effect of GOR, pressure and temperature on viscosity. One such extension is described in Hildebrand, J. H., and Scott, R. L., "The Solubility of Nonelectrolytes," 3rd ed., Reinhold, New York, (1950) as follows:

$$\left(\frac{\eta}{\eta_0}\right)_{live} = \left(\frac{\eta}{\eta_0}\right)_{STO}\left[\left(\frac{GOR_{s0}}{GOR_s}\right)^{1/3}\right]\left(\frac{T_0}{T}\right)^{4.5}\exp[9.6\times10^{-5}(P-P_0)], \quad (57)$$

where $$\left(\frac{\eta}{\eta_0}\right)_{STO}$$

is derived for stock tank conditions as described above, the pressures P and $P_0$ are calculated in psia, the temperatures T and $T_0$ are calculated in Rankine (R), and the gas-oil-ratios $GOR_s$ and $GOR_{s0}$ are calculated for the solution in scf/bbl.

The subscript 0 denotes the properties at the reference location. These corrections are similar to expressions given by Khan et al. in "Viscosity Correlations for Saudi Arabian Crude Oils," SPE Paper 15720, Fifth SPE Middle East Conference, Bahrain, Mar. 7-10, 1987 which determined that the viscosity of undersaturated oil is inversely proportional to $GOR_s^{1/3}$ and $T^{4.5}$.

In the case that the density calculation of Eqn. (54) is used to derive $$\left(\frac{\eta}{\eta_0}\right)_{STO}$$

for the live heavy oil viscosity calculations of Eqn. (53), the effects of GOR, pressure, and temperature on the density calculations of Eqn. (54) can be taken into account by:

$$\frac{\rho}{\rho_0} = \left(\frac{GOR_{s0}}{GOR_s}\right)^{\alpha}\exp[-\beta(T-T_0)]\exp[c_o(P-P_0)] \quad (58)$$

where $\alpha$ is a parameter, which can be set to a value such as 0.05;

$\beta$ is the isobaric thermal expansion coefficient of the fluid, which can be set to a value such as $5\times10^{-4}$ 1/K; and $c_o$ denotes compressibility, which can be set to a value such as $9\times10^{-6}$ 1/psia).

After step 273, the operations continue at step 283, as described further below.

In step 275, no suitable match has been found between the solubility curves and the measured properties. In this case, the operations can determine if there is a need for additional measurement stations and/or different methodologies for repeat processing and analysis in order to improve the confidence level of the measured and/or predicted fluid properties. For example, the measured and/or predicted properties of the reservoir fluid can be compared to a database of historical reservoir data to determine the measured and/or predicted properties make sense. If the data does not make sense, additional measurement station(s) or different methodologies (e.g., different model(s)) can be identified for repeat processing and analysis in order to improve the confidence level of the measured and/or predicted fluid properties.

Other factors can be used to determine if there is a need for additional measurement stations and/or different methodologies for repeat processing and analysis in order to improve the confidence level of the measured and/or predicted fluid properties. For example, in step 275, it is expected that the reservoir is compartmentalized or not in thermodynamic equilibrium. Thus, the measured fluid properties can be accessed to confirm that they correspond to this expected architecture.

If in step 275 there is a need for additional measurement stations and/or different methodologies, the operations can continue to step 277 to repeat the appropriate processing and analysis in order to improve the confidence level of the measured and/or predicted fluid properties.

If in step 275, there is no need for additional measurement stations and/or different methodologies (in other words, there is sufficient confidence level in the measured and/or predicted fluid properties), the operation continue to step 279 where the reservoir architecture is declared to be compartmentalized and/or not in thermodynamic equilibrium. Such a determination is supported by the invalidity of the assumptions of reservoir connectivity and thermal equilibrium that underlie the models utilized for predicting the solute part property gradient within the wellbore.

Subsequent to the determination of reservoir architecture in steps 257, 261, 265, 269, 273, and 279, the results of such determination are reported to interested parties in step 283. The characteristics of the reservoir architecture reported in step 283 can be used to model and/or understand the reservoir of interest for reservoir assessment, planning and management.

The computational analysis described herein can be carried out in real time with associated downhole fluid analysis or post job (subsequent to associated downhole fluid analysis) or prejob (prior to downhole fluid analysis).

The computational models and computational analysis described herein can also be integrated into reservoir simulation systems in order predict issues of asphaltene precipitation and tar formation over time during production of a reservoir in order to avoid such issues and optimize production over time.

There have been described and illustrated herein a preferred embodiment of a method, system and apparatus system for downhole fluid analysis of the fluid properties of a reservoir of interest and for characterizing the reservoir of interest based upon such downhole fluid analysis. While particular embodiments of the invention have been described, it is not intended that the invention be limited thereto, as it is intended that the invention be as broad in scope as the art will allow and that the specification be read likewise. Thus, while particular equations of state models, solubility models and applications of such models have been disclosed for predicting properties of reservoir fluid, it will be appreciated that other such models and applications thereof could be used as well. Moreover, the methodology described herein is not limited to stations in the same wellbore. For example, measurements from samples from different wells can be analyzed as described herein for testing for lateral connectivity. In addition, the workflow as described herein can be modified. For example, it is contemplated that other solute part classes (such as a solute class type including both asphaltene nanoaggregates and asphaltene clusters) can be defined. In another example, user input can select the solute type classes from a list of solute type classes for processing. The user might also be able to specify certain parameters for the processing, such as diameters that are used as input to the solubility model to derive concentration curves for the relevant solute part classes as well as optical density wavelengths that are used to correlate such concentrations to concentrations measured by downhole fluid analysis. It will therefore be appreciated by those skilled in the art that yet other modifications could be made to the provided invention without deviating from its spirit and scope as claimed.

What is claimed is:

1. A method for characterizing petroleum fluid in a reservoir traversed by at least one wellbore, the method comprising:
    (a) at a plurality of measurements stations within the at least one wellbore, acquiring via a borehole tool at least one fluid sample at the respective measurement station and performing via a data processing system of the borehole tool downhole fluid analysis of the fluid sample to measure properties of the fluid sample, the properties including concentration of a plurality of high molecular weight components;
    (b) for each given one of a plurality of class-types corresponding to different subsets of a predetermined set of high molecular weight components, using a model of the a data processing system that predicts concentration of the high molecular weight components of the given class-type for said plurality of measurement stations;
    (c) comparing via the data processing system the predicted concentrations of the high molecular weight components for the plurality of class-types as derived in (b) with corresponding concentrations measured by the downhole fluid analysis in (a) for said plurality of measurement stations to identify the best matching class-type;
    (d) in the event that the best-matching class type identified in (c) corresponds to at least one predetermined asphaltene component, evaluating via the data processing system asphaltene stability in the petroleum fluid of the reservoir at a given depth in the reservoir using equilibrium criteria involving an oil rich phase and an asphaltene rich phase of respective components of the petroleum fluid at the given depth, wherein the equilibrium criteria of (d) are defined by a relationship of the form $$x_i^{oil}\gamma_i^{oil} = x_i^{asph}\gamma_i^{asph},$$

where the subscript i corresponds to the respective component of the petroleum fluid of the reservoir at the given depth,
superscripts oil and asph correspond to the oil rich phase and the asphaltene rich phase, respectively, of component i at the given depth,
$x_i^{oil}$ is the mole fraction of the oil rich phase of component i of the petroleum fluid of the reservoir at the given depth,
$\gamma_i^{oil}$ is the activity coefficient of the oil rich phase of component i of the petroleum fluid of the reservoir at the given depth,
$x_i^{asph}$ is the mole fraction of the asphaltene rich phase of component i of the petroleum fluid of the reservoir at the given depth, and
$\gamma_i^{asph}$ is the activity coefficient of the asphaltene rich phase of component i of the petroleum fluid of the reservoir at the given depth, and wherein the equilibrium criteria of (d) are further defined by a relationship of the form:

$$\sum_{i=1}^{N} x_i^{asph} - \sum_{i=1}^{N} x_i^{oil} = \sum_{i=1}^{N} \frac{(K_i - 1)}{(L + (1 - L)K_i)} z_i = 0$$

where $K_i = x_i^{asph}/x_i^{oil} = \gamma_i^{oil}/\gamma_i^{asph}$, $K_i$ is an equilibrium constant of component i,
L is mole fraction of the oil rich phase of all N components of the petroleum fluid of the reservoir at the given depth, and
$z_i$, is the mole fraction of the mixture of the oil rich phase and asphaltene rich phase of component i at the given depth; and
(e) using the results of (d) for reservoir analysis.

2. A method according to claim 1, wherein:
the evaluation of (d) is carried out over multiple depths of the reservoir.

3. A method according to claim 1, wherein:
the oil rich phase mole fractions $x_i^{oil}$ for the components of the petroleum fluid of the reservoir are used as inputs to a first solubility model that solves for the activity coefficient $\gamma_i^{oil}$ of the oil rich phase of component i of the petroleum fluid of the reservoir at the given depth; and
the asphaltene mole fractions $x_i^{asph}$ for the components of the petroleum fluid of the reservoir are used as inputs to a second solubility model that solves for the activity coefficient $\gamma_i^{asph}$ of the asphaltene rich phase of component i of the reservoir fluid at the given depth.

4. A method according to claim 3, wherein:
the first solubility model is of the form $$\ln \gamma_i^{oil} = \ln\left(\frac{\phi_i^{oil}}{x_i^{oil}}\right) + 1 - \frac{v_i^{oil}}{v^{oil}} + \frac{v_i^{oil}}{RT}(\delta_i^{oil} - \delta^{oil})^2,$$

where $\phi_i^{oil}$ is the volume fraction of the oil rich phase of component i at the given depth,
$v_i^{oil}$ is the partial molar volume of the oil rich phase of component i at the given depth,
$v_{oil}$ is the molar volume for the oil rich phase for all components at the given depth,
$\delta_i^{oil}$ is the solubility parameter for the oil rich phase of component i at the given depth,
$\delta_{oil}$ is the solubility parameter for the oil rich phase of all components at the given depth, R is the universal gas constant, and
T is the absolute temperature of the petroleum fluid of the reservoir at the given depth; and
the second solubility model is of the form $$\ln \gamma_i^{asph} = \ln\left(\frac{\phi_i^{asph}}{x_i^{asph}}\right) + 1 - \frac{v_i^{asph}}{v^{asph}} + \frac{v_i^{asph}}{RT}\left(\delta_i^{asph} - \delta^{asph}\right)^2,$$

where $\phi_i^{asph}$ is the volume fraction of the asphaltene rich phase of component i at the given depth,
$v_i^{asph}$ is the partial molar volume of the asphaltene rich phase of component i at the given depth,
$v^{asph}$ is the molar volume for the asphaltene phase for all components at the given depth,
$\delta_i^{asph}$ is the solubility parameter for the asphaltene rich phase of component i at the given depth, S
$\delta_{asph}$ is the solubility parameter for the oil rich phase of all components at the given depth,
R is the universal gas constant, and
T is the absolute temperature of the petroleum fluid of the reservoir at the given depth.

5. A method according to claim 1, wherein:
in (e), the criteria results of (d) are used to: determine reservoir architecture, confirm the instability of asphaltenes and possible implications of such instability during production, determine whether or not the reservoir is compartmentalized and/or in thermal equilibrium, or a combination thereof.

6. A method according to claim 1, wherein: in (e), the results of (d) are used to as a criterion to perform additional sampling and analysis of petroleum fluid of the reservoir, and wherein the additional sampling and analysis of petroleum fluid of the reservoir involves at least one of
i) collection of core samples where asphaltenes might be destabilized to ascertain whether solid asphaltenes are in the core samples;
ii) collection of live oil samples for downhole fluid analysis and analysis of onset pressure of asphaltene precipitation;
iii) collection of core samples or live oil samples or gas samples for geochemistry analysis to ascertain whether a late stage of gas charging occurred in the reservoir;
iv) collection of core samples or live oil samples for analysis to confirm the implication of potential flow assurance problems during production; and
v) collection of core samples or live oil samples for analysis to confirm the implication of a significant viscosity increase in the petroleum fluid of the reservoir as a function of depth.

7. A method according to claim 1, further comprising:
(f) inputting fluid sample properties measured in (a) to an equation of state model to predict compositional properties and fluid properties at different locations within the reservoir; and
(g) tuning the equation of state model of (f) based on fluid sample properties measured in (a).

8. A method according to claim 7, wherein:
the equation of state model of (e) is used to derive inputs for the model of (b).

9. A method according to claim 1, wherein:
the model of (b) is a solubility model that characterizes relative concentrations of a set of high molecular weight components as a function of depth as related to relative solubility, density and molar volume of the high molecular weight components of the set at varying depth; and
the solubility model treats the reservoir fluid as a mixture of two parts, the two parts being a solute part and a solvent part, the solute part comprising the set of high molecular weight components.

10. A method according to claim 9, wherein:
the high molecular weight components of the solute part are selected from the group including resins, asphaltene nanoaggregates, and asphaltene clusters.

11. A method according to claim 9, wherein:
the model of (b) is based on a mathematical relationship of the form $$\frac{\phi_i(h_2)}{\phi_i(h_1)} = \exp\left\{\frac{v_i g(\rho_m - \rho_i)(h_2 - h_1)}{RT} + \left(\frac{v_i}{v_m}\right)_{h_2} - \left(\frac{v_i}{v_m}\right)_{h_1} - \frac{v_i\left[(\delta_i - \delta_m)_{h_2}^2 - (\delta_i - \delta_m)_{h_1}^2\right]}{RT}\right\}$$

where $\phi_i(h_1)$ is the volume fraction for the solute part at depth $h_1$,
$\phi_i(h_2)$ is the volume fraction for the solute part at depth $h_2$,
$v_i(h_2)$ is the partial molar volume for the solute part,
$v_m$ is the molar volume for the solvent part,
$\delta_i$ is the solubility parameter for the solute part,
$\delta_m$ is the solubility parameter for the solvent part,
$\rho_i$ is the partial density for the solute part,
$\rho_m$ is the density for the solute part,
R is the universal gas constant, and
T is the absolute temperature of the reservoir fluid.

12. A method according to claim 9, wherein:
for a number of different class-type solute parts, the solubility model is used to generate a plurality of concentration curves corresponding to the respective class-type solute part and a range of molar volumes associated with the respective class-type solute part.

13. A method according to claim 9, wherein:
the properties measured in (a) include live fluid density for the respective fluid sample; and
the model of (b) predicts concentration of at least one high molecular weight component of the petroleum fluid for said plurality of measurement stations based upon solubility parameter inputs derived according to a linear relation that relates solubility to live fluid density measured in (a).

14. A method according to claim 1, wherein:
in (e), the criteria results of (d) are used as part of a workflow to determine stability of asphaltene clusters in the petroleum fluid of the reservoir; and
in the event that the workflow determines there is stable asphaltene clusters in the petroleum fluid of the reservoir, using a viscosity model to characterize the viscosity of the petroleum fluid of the reservoir as a function of depth.

15. A method according to claim 14, wherein:
the viscosity model is of the form $$\frac{\eta}{\eta_0} = \left[\frac{1 - K' \cdot A}{1 - K' \cdot A_0}\right]^{-v}$$

where $\eta$ is the viscosity of the petroleum fluid of the reservoir at a given depth;

$\eta_0$ is the viscosity of the petroleum fluid of the reservoir at a reference location;

v is a shape factor parameter;

K' is a solvation constant represented by $$\frac{\rho}{\rho_a} K,$$

where $\rho$ and $\rho_a$ are the densities of oil mixtures and asphaltenes, respectively, at the given depth and K is a solvation constant; and A is the weight fraction of asphaltenes (clusters) at the given depth, and $A_0$ is the weight fraction of asphaltenes (clusters) at the reference location.

16. A method according to claim 14, wherein:

the viscosity model is of the form $$\frac{\eta}{\eta_0} = \exp\left[[\eta]\left(\frac{A}{1-\frac{A}{A_{max}}} - \frac{A_0}{1-\frac{A_0}{A_{max}}}\right)\right]$$

where $\eta$ is the viscosity of the petroleum fluid of the reservoir at a given depth;

$\eta_0$ is the viscosity of the petroleum fluid of the reservoir at a reference location;

$[\eta]$ is the intrinsic viscosity;

A is the weight fraction of asphaltenes (clusters) at a given depth;

$A_0$ is the weight fraction of asphaltenes (clusters) at a reference location; and $A_{max}$ is a parameter.

17. A method for characterizing petroleum fluid in a reservoir traversed by at least one wellbore, the method comprising:

(a) determining via a data processing system of a borehole tool concentration of a set of components of the petroleum fluid as a function of depth in the reservoir, wherein the set of components include at least one asphaltene component;

(b) evaluating via the data processing system asphaltene stability in the reservoir fluid at a given depth in the reservoir using equilibrium criteria involving an oil rich phase and an asphaltene rich phase of respective components of the petroleum fluid at the given depth, wherein the equilibrium criteria are based upon the component concentrations for the given depth as determined in (a), wherein the equilibrium criteria of (b) are defined by a relationship of the form $$x_i^{oil} \gamma_i^{oil} = x_i^{asph} \gamma_i^{asph},$$

where the subscript i corresponds to the respective component of the petroleum fluid of the reservoir at the given depth, superscripts oil and asph correspond to the oil rich phase and the asphaltene rich phase, respectively, of component i at the given depth, $x_i^{oil}$ is the mole fraction of the oil rich phase of component i of the petroleum fluid of the reservoir at the given depth, $\gamma_i^{oil}$ is the activity coefficient of the oil rich phase of component i of the petroleum fluid of the reservoir at the given depth, $x_i^{asph}$ is the mole fraction of the asphaltene rich phase of component i of the petroleum fluid of the reservoir at the given depth, and $\gamma_i^{asph}$ is the activity coefficient of the asphaltene rich phase of component i of the petroleum fluid of the reservoir at the given depth, and wherein the equilibrium criteria of (d) are further defined by a relationship of the form:

$$\sum_{i=1}^{N} x_i^{asph} - \sum_{i=1}^{N} x_i^{oil} = \sum_{i=1}^{N} \frac{(K_i - 1)}{(L + (1-L)K_i)} z_i = 0$$

where $K_i = x_i^{asph}/x_i^{oil} = \gamma_i^{oil}/\gamma_i^{asph}$, $K_i$ is an equilibrium constant of component i, L is mole fraction of the oil rich phase of all N components of the petroleum fluid of the reservoir at the given depth, and $z_i$ is the mole fraction of the mixture of the oil rich phase and asphaltene rich phase of component i at the given depth; and (c) using the results of (b) for reservoir analysis.

18. A method according to claim 17, wherein the component concentrations of (a) are or derived from downhole fluid analysis, derived according to an equation of state model.

* * * * *